(12) United States Patent
Gu et al.

(10) Patent No.: US 11,351,230 B2
(45) Date of Patent: Jun. 7, 2022

(54) PATCH LOADED WITH DUAL-SENSITIVE VESICLES FOR ENHANCED GLUCOSE-RESPONSIVE INSULIN DELIVERY

(71) Applicant: North Carolina State University, Raleigh, NC (US)

(72) Inventors: Zhen Gu, Apex, NC (US); Jicheng Yu, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 49 days.

(21) Appl. No.: 16/347,536

(22) PCT Filed: Nov. 7, 2017

(86) PCT No.: PCT/US2017/060325
§ 371 (c)(1),
(2) Date: May 3, 2019

(87) PCT Pub. No.: WO2018/085809
PCT Pub. Date: May 11, 2018

(65) Prior Publication Data
US 2020/0330562 A1 Oct. 22, 2020

Related U.S. Application Data

(60) Provisional application No. 62/418,509, filed on Nov. 7, 2016.

(51) Int. Cl.
*A61K 9/00* (2006.01)
*A61K 38/28* (2006.01)
(Continued)

(52) U.S. Cl.
CPC .......... *A61K 38/443* (2013.01); *A61K 9/0021* (2013.01); *A61K 9/5146* (2013.01);
(Continued)

(58) Field of Classification Search
None
See application file for complete search history.

(56) References Cited

U.S. PATENT DOCUMENTS 6,960,617 B2 11/2005 Omidian et al.
2002/0197261 A1 12/2002 Li et al.
(Continued)

FOREIGN PATENT DOCUMENTS

AU 2016252738 10/2021
CN 104353062 A 2/2015
(Continued)

OTHER PUBLICATIONS

Yu et al. (PNAS 2015; 112(27):8260-8265). (Year: 2015).*
(Continued)

*Primary Examiner* — Ernst V Arnold
(74) *Attorney, Agent, or Firm* — Jenkins, Wilson, Taylor & Hunt, P.A.

(57) ABSTRACT

A composition comprising an amphiphilic polymeric material that is both hydrogen peroxide- and hypoxia-sensitive is described. The composition can further include a glucose-oxidizing enzyme and insulin, a bioactive derivative thereof, and/or another therapeutic agent (e.g., another diabetes treatment agent). The polymeric material can form vesicles that comprise single or multiple layers of the polymeric material that enclose the glucose-oxidizing enzyme and the insulin, bioactive derivative and/or other therapeutic agent. The vesicles can be loaded into microneedles to, for example, prepare microneedle arrays for skin patches. Methods of delivering insulin to a subject using the compositions, vesicles, microneedles, and/or microneedle array skin patches are also described.

35 Claims, 15 Drawing Sheets

(51) Int. Cl.
| | |
|---|---|
| A61K 38/44 | (2006.01) |
| A61K 9/51 | (2006.01) |
| A61K 9/70 | (2006.01) |
| A61M 37/00 | (2006.01) |

(52) U.S. Cl.
CPC ............ *A61K 9/7084* (2013.01); *A61K 38/28* (2013.01); *A61M 37/0015* (2013.01); *C12Y 101/03004* (2013.01); *A61M 2037/0023* (2013.01); *A61M 2037/0053* (2013.01); *A61M 2037/0061* (2013.01)

(56) References Cited

U.S. PATENT DOCUMENTS

| | | |
|---|---|---|
| 2004/0265386 A1 | 12/2004 | Taylor |
| 2008/0102114 A1 | 5/2008 | Koritala et al. |
| 2010/0276319 A1 | 11/2010 | Clarke |
| 2011/0177139 A1 | 7/2011 | Jung et al. |
| 2012/0046651 A1 | 2/2012 | Beyer et al. |
| 2015/0030641 A1 | 1/2015 | Anderson et al. |
| 2018/0110841 A1 | 4/2018 | Gu et al. |
| 2018/0333495 A1 | 11/2018 | Matsumoto et al. |

FOREIGN PATENT DOCUMENTS

| | | |
|---|---|---|
| CN | 107530296 B | 6/2021 |
| EP | 3285750 | 10/2021 |
| HK | 1245105 | 4/2021 |
| IN | 378574 | 4/2021 |
| JP | 2005-083928 | 3/2005 |
| JP | 6856546 | 3/2021 |
| NG | NG/PT/C/2017/2447 | 3/2018 |
| RU | 2719584 | 4/2020 |
| WO | WO 2007/012114 A1 | 2/2007 |
| WO | WO 2007/075388 A2 | 7/2007 |
| WO | WO 2010/040271 A1 | 4/2010 |
| WO | WO 2010/088300 A1 | 8/2010 |
| WO | WO 2012/050179 | 4/2012 |
| WO | WO 2013/123492 A2 | 8/2013 |
| WO | WO 2014/179344 A1 | 11/2014 |
| WO | WO 2016/172320 A1 | 10/2016 |
| WO | WO 2017/143153 A1 | 8/2017 |

OTHER PUBLICATIONS

Advisory Action corresponding to U.S. Appl. No. 15/567,532 dated Oct. 11, 2019.
Aronoff et al. (1975) Complexation of D-glucose with borate. Carbohydr. Res. 40(2):299-309.
Bariya et al., "Microneedles: an emerging transdermal drug delivery system," Journal of Pharmacy and Pharmacology, vol. 64, pp. 11-29 (2011).
Beers et al. (1952), "A Spectrophotometric Method for Measuring the Breakdown of Hydrogen Peroxide By Catalase," J. Biol. Chem. 195(1):133-140.
Bratlie et al. (2012) Materials for diabetes therapeutics. Advanced Healthcare Materials 1(3): 267-284.
Chen et al., "Glucose-Responsive Microneedle Patches for Diabetes Treatment," Journal of Diabetes Science and Technology, vol. 13(1), pp. 41-48 (2019).
Chou et al. (2015), "Glucose-responsive insulin activity by covalent modification with aliphatic phenylboronicacid conjugates," Proc. Natl. Acad. Sci. USA, 112(8):2401-2406.
Chu et al. (2012), "In vitro and in vivo testing of glucose-responsive insulin-delivery microdevices in diabetic rats," The Royal Society of Chemistry, vol. 12, No. 14, pp. 2533-2539.
Communication of European publication number and information on the application of Article 67(3) EPC corresponding to European Patent Application No. EP16783841.6 dated Jan. 31, 2018.
Dowd et al. (1983) Measurement of transcutaneous oxygen pressure in health and peripheral arterial occlusive disease. Journal of Bone and Joint Surgery, British vol. 65-B(1):79-83.

Edwards (1993) Nitroimidazole drugs—action and resistance mechanisms. I. Mechanisms of action. J. Antimicrob. Chemother. 31(1):9-20.
Examination Report corresponding to Australian application No. 2016252738 dated Jul. 9, 2020.
Extended European Search Report corresponding to European Patent Application Serial No. 16783841.6 dated Nov. 12, 2018.
Fercher et al. (2011) Intracellular O2 Sensing Probe Based on Cell-Penetrating Phosphorescent Nanoparticles. Acs Nano 5(7):5499-5508.
Fischel-Ghodsian et al. (1988), "Enzymatically controlled drug delivery," Proc. Natl. Acad. Sci. USA, 85(7): 2403-2406.
Fletcher (1980) On Facilitated Oxygen Diffusion in Muscle Tissues. Biophys. J. 29(3):437-458.
Gilroy et al. (2016) "Controlled Release of Biologies for the Treatment of Type 2 Diabetes," Author Manuscript, published in final edited form in J. Controlled Release, vol. 240, pp. 151-164 http.//dx.doi.org/10.1016/j.jconrel.2015/12/002 (14 pages).
Gordijo et al. (2011) Nanotechnology-Enabled Closed Loop Insulin Delivery Device: In Vitro and In Vivo Evaluation of Glucose-Regulated Insulin Release for Diabetes Control. Adv. Funct. Mater. 21(1):73-82.
Grant Decision corresponding to Kazakhstan Patent Application No. 20171060.1 dated May 13, 2019.
Gu et al., "Glucose-Responsive Microgels Integrated with Enzyme Nanocapsules for Closed-Loop Insulin Delivery," ACS-Nano, vol. 7, No. 8, pp. 6758-6766 (2013).
Gu et al. (2013) Injectable Nano-Network for Glucose-Mediated Insulin Delivery. ACS Nano 7(5):4194-4201.
Heo et al. (2011) "Long-term In Vivo Glucose Monitoring using Fluorescent Hydrogel Fibers," Proc. Natl. Acad. Sci USA 108(33):13399-13403.
Intent to Grant corresponding to European Application No. 16783841.6 dated May 25, 2020.
IPRP corresponding to International Patent Application Serial No. PCT/US2016/028605 dated Oct. 24, 2017.
Kataoka et al. (1998) Totally Synthetic Polymer Gels Responding to External Glucose Concentration: Their Preparation and Application to On-Off Regulation of Insulin Release. J. Am. Chem. Soc. 120(48):12694-12695.
Kim et al. (1990) Self-regulated glycosylated insulin delivery. J. Controlled Release 11 (1):193-201.
Krohn et al. (2008) Molecular imaging of hypoxia. J. Nucl. Med. 49(Suppl. 2):129S-148S.
Lee et al., "Nanoparticle popsicle: Transdermal delivery of nanoparticles using polymeric microneedle array," Korean Journal of Chemical Engineering, vol. 28, No. 9, pp. 1913-1917 (2011).
Ling & Chen (2013) Dissolving polymer microneedle patches for rapid and efficient transdermal delivery of insulin to diabetic rats. Acta Biomaterialia 9:8952-8961.
Liu et al. (2013) "Biomimetic enzyme nanocomplexes and their use as antidotes and preventive measures for alcohol intoxication," Nat. Nanotechnol. 8(3):187-192.
Martanto et al. (2004) Transdermal delivery of insulin using microneedles in vivo. Pharmaceutical Research 21(6):947-952.
Michaels et al. (1975) Drug permeation through human skin. Theory and in vitro experimental measurements. AIChE J 21(5):985-996.
MIT Technology Review, "35 Innovators Under 35," https://www.technologyreview.com/lists/innovators-under-35/2015/, pp. 1-11 (2015) [retrieved online Nov. 11, 2019].
Mo et al. (2014) Emerging micro- and nanotechnology based synthetic approaches for insulin delivery. Chemical Society Reviews 43(10):3595-3629.
Narayan (2014) Transdermal Delivery of Insulin via Microneedles. J. Biomedical Nanotechnology 10:2244-2260.
Notice of Acceptance corresponding to Nigerian Patent Application No. NGPCT20172447 dated Dec. 19, 2017.
Notice of Allowance corresponding to U.S. Appl. No. 15/567,532 dated Aug. 19, 2020.
Notification Concerning Availability of the Publication of the International Application corresponding to International application No. PCT/US2016/028605 dated Oct. 27, 2016.

(56) References Cited

OTHER PUBLICATIONS

Notification of Transmittal of the International Search Report and the Written Opinion of the International Searching Authority, or the Declaration corresponding to International application No. PCT/US2016/028605 dated Jul. 15, 2017.
Notification of Transmittal of the International Search Report and the Written Opinion of the International Searching Authority, or the Declaration corresponding to International application No. PCT/US2017/060325 dated Jan. 11, 2018.
Notification of Transmittal of International Preliminary Report on Patentability (Chapter I of the Patent Cooperation Treaty) corresponding to International application No. PCT/US2017/060325 dated May 16, 2019.
Nunn et al. (1995) Nitroimidazoles and imaging hypoxia. Eur. J. Nucl. Med. 22(3):265-280.
Office Action corresponding to Colombian Patent Application Serial No. NC2017/0011422 dated Nov. 17, 2017.
Office Action (Restriction Requirement) corresponding to U.S. Appl. No. 15/567,532 dated Nov. 21, 2018.
Office Action corresponding to Panama Patent Application Serial No. 9181601 dated Jul. 17, 2018.
Office Action corresponding to Israeli Patent Application Serial No. 255155 dated Aug. 15, 2018.
Office Action (Notice of Opposition) corresponding to Ecuador Patent Application Serial No. 2017-73558 dated Dec. 3, 2018.
Office Action corresponding to Columbian Patent Application Serial No. NC2017/0011422 dated Jan. 14, 2019.
Office Action corresponding to U.S. Appl. No. 15/567,532 dated Mar. 11, 2019.
Office Action corresponding to Israeli Patent Application No. 255155 dated May 5, 2019.
Office Action corresponding to U.S. Appl. No. 15/567,532 dated Jun. 14, 2019.
Office Action (Technical Examination) corresponding to Columbian Patent Application No. NC2017/0011422 dated Jun. 18, 2019.
Office Action corresponding to Russian Patent Application No. 2017139931 dated Dec. 13, 2019.
Office Action corresponding to Chilean Patent Application No. 2017-002652 dated Jan. 20, 2020.
Office Action corresponding to U.S. Appl. No. 15/567,532 dated Feb. 3, 2020.
Office Action corresponding to Indian Patent Application No. 201727037788 dated Feb. 11, 2020.
Office Action (Notice of Reason for Rejection) corresponding to Japanese Patent Application No. 2017-555709 dated Mar. 9, 2020.
Decision to Grant corresponding to Russian Patent Application No. 2017139931 dated Feb. 6, 2020.
Office Action corresponding to U.S. Appl. No. 15/567,532 dated May 21, 2020.
Office Action corresponding to Mexican Patent Application Serial No. 2017/013337 dated Jul. 14, 2020.
Owens et al. (2001) Insulins today and beyond. Lancet 358(9283):739-746.
Pickup et al. (2008) Nanomedicine and its potential in diabetes research and practice. Diabetes-Metabolism Research and Reviews 24(8):604-610.
Podual et al. (2000) "Preparation and dynamic response of cationic copolymer hydrogels containing glucose oxidase," Polymer 41(11):3975-3983.
Prausnitz (2004) "Microneedles for transdermal drug delivery," Adv. Drug Deliv., Rev. 56(5):581-587.
Prausnitz & Langer (2008) Transdermal drug delivery. Nature Biotechnology 26(11):1261-1268.
Ravaine et al. (2008) Chemically controlled closed-loop insulin delivery. Journal of Controlled Release 132:2-11.
Rogers, "Top 10 images of 2015," ScienceMag.org, https://www.sciencemag.org/news/2015/12/top-10-images-2015 dated Dec. 23, pp. 1-16, 2015 [retrieved online Nov. 11, 2019].

Saravanakumar et al., "Reactive-oxygen-species-responsive drug delivery systems: promises and challenges," Advanced Science, 4:1600124 (Jun. 8, 2016) (pp. 1-19).
Stumvoll et al. (2005) Type 2 diabetes: principles of pathogenesis and therapy. Lancet 365(9467):1333-1346.
Tabák et al. (2012) Prediabetes: a high-risk state for diabetes development. Lancet 379(9833):2279-2290.
Tai et al. (2014) "Bio-inspired synthetic nanovesicles for glucose-responsive release of insulin," Biomacromolecules 15(10): 3495-3502.
Takasawa et al. (2008) Applications of Nitroimidazole In Vivo Hypoxia Imaging in Ischemic Stroke. Stroke 39(5):1629-1637.
Takiyama and Haneda (2014) Hypoxia in Diabetic Kidneys. BilMed Research International 1-10.
Thambi et al. (2014) Hypoxia-responsive polymeric nanoparticles for tumor-targeted drug delivery. Hindawi. Biomaterials 35(5):1735-1743.
Tiegs et al. (1992) A T cell-dependent experimental liver injury in mice inducible by concanavalin A.J. Clin. Invest. 90(1):196.
Veiseh et al. (2015) Managing diabetes with nanomedicine: challenges and opportunities. Nature Reviews Drug Discovery 14(1):45-57.
Veiseh et al. (2015) "A smart insulin patch," Nature, vol. 524, pp. 39-40.
Wang et al., "Glucose-Responsive Insulin and Delivery Systems: Innovation and Translation," Advanced Materials, 1902004, pp. 1-19 (2019).
Will et al. (2006) Analysis of mitochondrial function using phosphorescent oxygen-sensitive probes. Nat. Protoc. 1:2563-2572.
Wu et al. (2011) Organization of Glucose-Responsive Systems and Their Properties. Chem. Rev. 111(12):7855-7875.
Yang et al. (2013) A bio-inspired swellable microneedle adhesive for mechanical interlocking with tissue. Nature Communications 4:1-10.
Yu et al. (2015) Microneedle-array patches loaded with hypoxia-sensitive vesicles provide fast glucose-responsive insulin delivery. PNAS 112(27):8260-8265.
Yu et al., "Stimuli-responsive delivery of therapeutics for diabetes treatment," Bioengineering & Translational Medicine, 1:323-337 (Oct. 3, 2016).
Zhang et al., "Design and fabrication of MEMS-based microneedle arrays for medical applications," Microsystem Technologies, vol. 15, Iss. 7, pp. 1073-1082 (2009).
Bonnet et al. "Novel nitroimidazole alkylsulfonamides as hypoxic cell radiosensitisers," Bioorg, Med. Chem. vol. 22, pp. 2123-2132 (2014).
Decision to Grant corresponding to European Patent Application No. EP16783841.6 dated Sep. 24, 2020.
Decision to Grant corresponding to Japanese Patent Application No. 2017-555709 dated Feb. 22, 2021.
Examination Report corresponding to Indonesian Patent Application No. PID201708190 dated Jun. 14, 2021.
European Search Report corresponding to European Patent Application Serial No. 20202740 dated Feb. 19, 2021.
Kang et al. "A sulfonamide based glucose-responsive hydrogel with covalently immobilized glucose oxidase and catalase," J. Controlled Release vol. 86, pp. 115-121 (2003).
Kohen, R., "Skin antioxidants: their role in aging and in oxidative stress—new approaches for their evaluation," Biomed. Pharmacother. vol. 53, pp. 181-192 (1999).
Liu et al., "Preparation and characterization of novel hyaluronic acid microneedles for insulin transdermal delivery," Journal of Shenyang Pharmaceutical University, vol. 27, No. 1, pp. 6-11 (2010).
Makino et al., "A Microcapsule self-regulating delivery system for insulin," J. Controlled Release, vol. 12 pp. 235-239 (1990).
Matsumoto et al. "High Index Resist for 193 nm Immersion Lithography," Macromolecules vol. 41, pp. 5674-5680 (2008).
Matsumoto, Miyahara, "Artificial Pancreas" of a Fully Synthetic Type, Using a Smart Gel,, Smart Human Sensing, CMC Publishing Company, 2014, pp. 233-240 (English Translation and Written in Japanese).

(56) References Cited

OTHER PUBLICATIONS

Napoli et al. "Oxidation-responsive polymeric vesicles," Nat. Mater. vol. 3, pp. 183-189 (2004).
Napoli et al., "New Synthetic Methodologies for Amphiphilic Multiblock Copolymers of Ethylene Glycol and Propylene Sulfide," Macromolecules, vol. 34, pp. 8913-8917 (2001).
Notice of Allowance corresponding to U.S. Appl. No. 15/567,532 dated Jul. 20, 2021.
Notice of Allowance corresponding to U.S. Appl. No. 15/567,532 dated Apr. 6, 2021.
Notice of Acceptance corresponding to Australian Patent Application No. 2016252738 dated Jun. 21, 2021.
Notice of Publication corresponding to European Patent Application No. 20202740 dated Feb. 21, 2021.
Notice of Grant corresponding to Mexican Patent Application Serial No. 2017013337 dated Feb. 11, 2021.
Notice of Issuance corresponding to Chinese Patent Application Serial No. 201680023377.6 dated Mar. 19, 2021.
Hearing Notice corresponding to Indian Patent Application No. 2017237037788 dated Feb. 26, 2021.
Office Action corresponding to Vietnamese Patent Application Serial No. 1-2017-04619 dated Feb. 24, 2021.
Office Action corresponding to Philippines Patent Application Serial No. 12017501910 dated Dec. 1, 2020.
Office Action (Notice of Reason for Rejection) corresponding to Japanese Patent Application No. 2017-555709 dated Oct. 26, 2020.
Office Action corresponding to Ukranian Patent Application No. 2017-10540 dated Nov. 16, 2020.
Office Action corresponding to Chinese Patent Application No. 2016800233776 dated Nov. 9, 2020.
Office Action corresponding to Australian Patent Application No. 2016252738 dated Nov. 24, 2020.
Ohkubo et al., "Intensive insulin therapy prevents the progression of diabetic microvascular complications in Japanese patients with non-insulin-dependent disbetes mellitus: a randomized prospective 6-year study," Diabetes Res. Clin. Pract., vol. 28, pp. 103-117 (1995).
Pickup (2012) "Insulin-pump therapy for type 1 diabetes mellitus," New Engl. J. Med., 366(17): 1616-1624.
Podual et al., "Glucose-sensitivity of glucose oxidase-containing cationic copolymer hydrogels having poly(ethylene glycol) grafts," J. Controlled Release, vol. 67,pp. 9-17 (2000).
Seki et al., "Accumulation of 2-aminoimidazole by *Streptomyces eurocidicus*," J Biochem, vol. 67, pp. 389-396 (1970).
Tang et al., "Water-Soluble Poly(L-serine)s with Elongated and Charged Side-Chains: Synthesis, Conformations and Cell-Penetrating Properties," Biomacromolecules, vol. 13, pp. 2609-2615 (2012).
Traitel et al., "Characterization of glucose-sensitive insulin release systems in simulated in vivo conditions," Biomaterials vol. 21, pp. 1679-1687 (2000).
Zhang et al., "Modulated insulin permeation across a glucose-sensitive polymeric composite membrane," J. Controlled Release vol. 80, pp. 169-178 (2002).
Issue Notification corresponding U.S. Appl. No. 15/567,532 dated Dec. 7, 2021.

\* cited by examiner

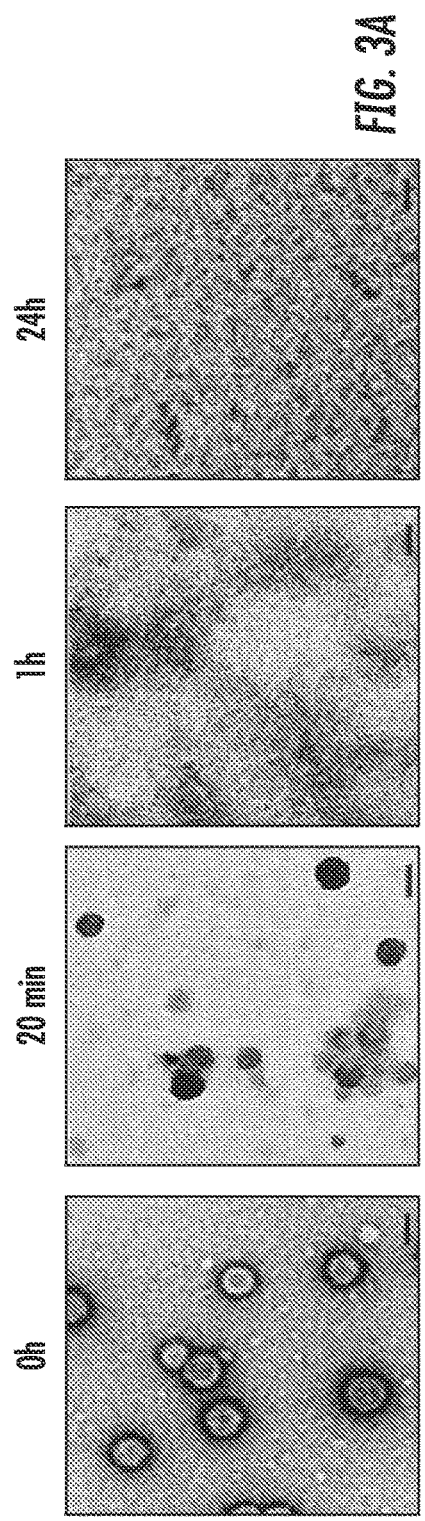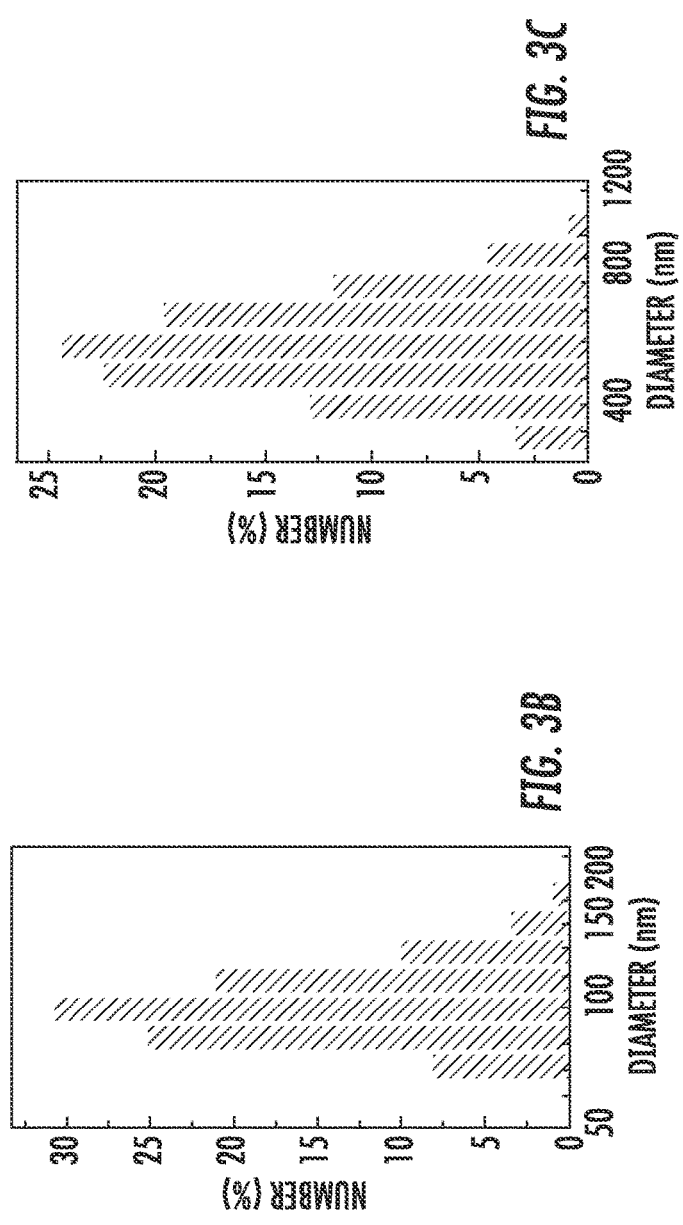
FIG. 3A
FIG. 3B
FIG. 3C

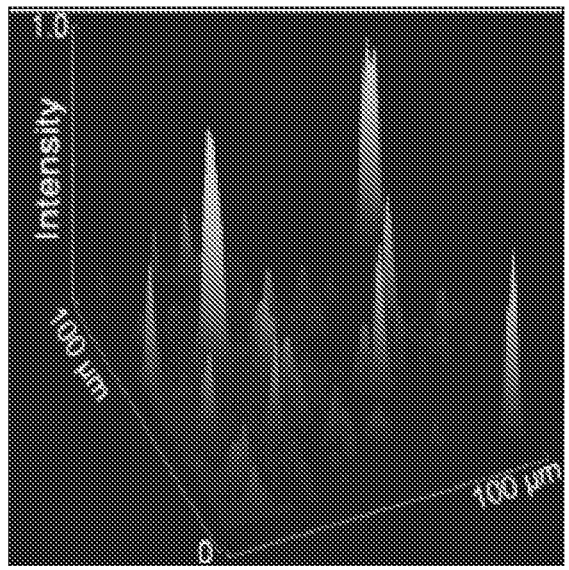
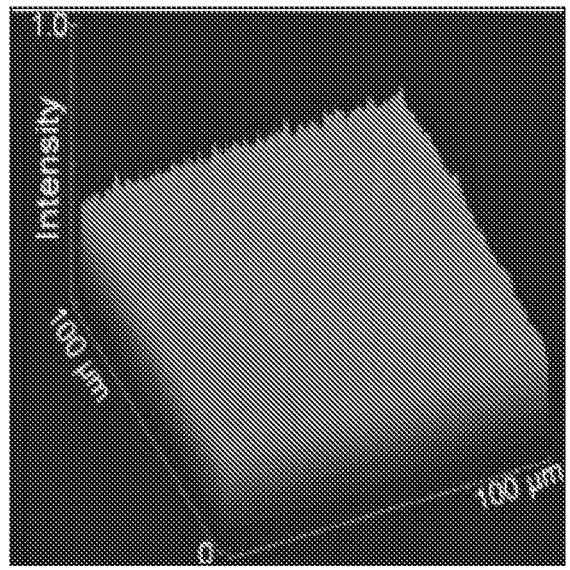
FIG. 3D          FIG. 3E
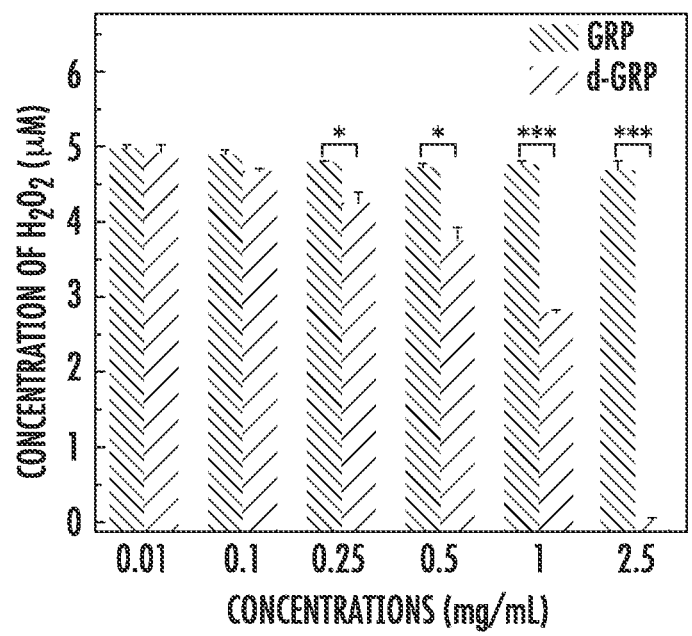
FIG. 3F

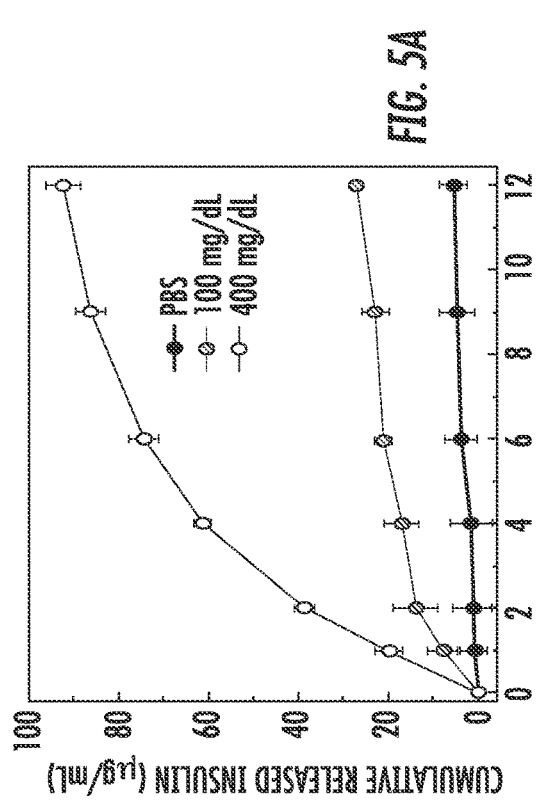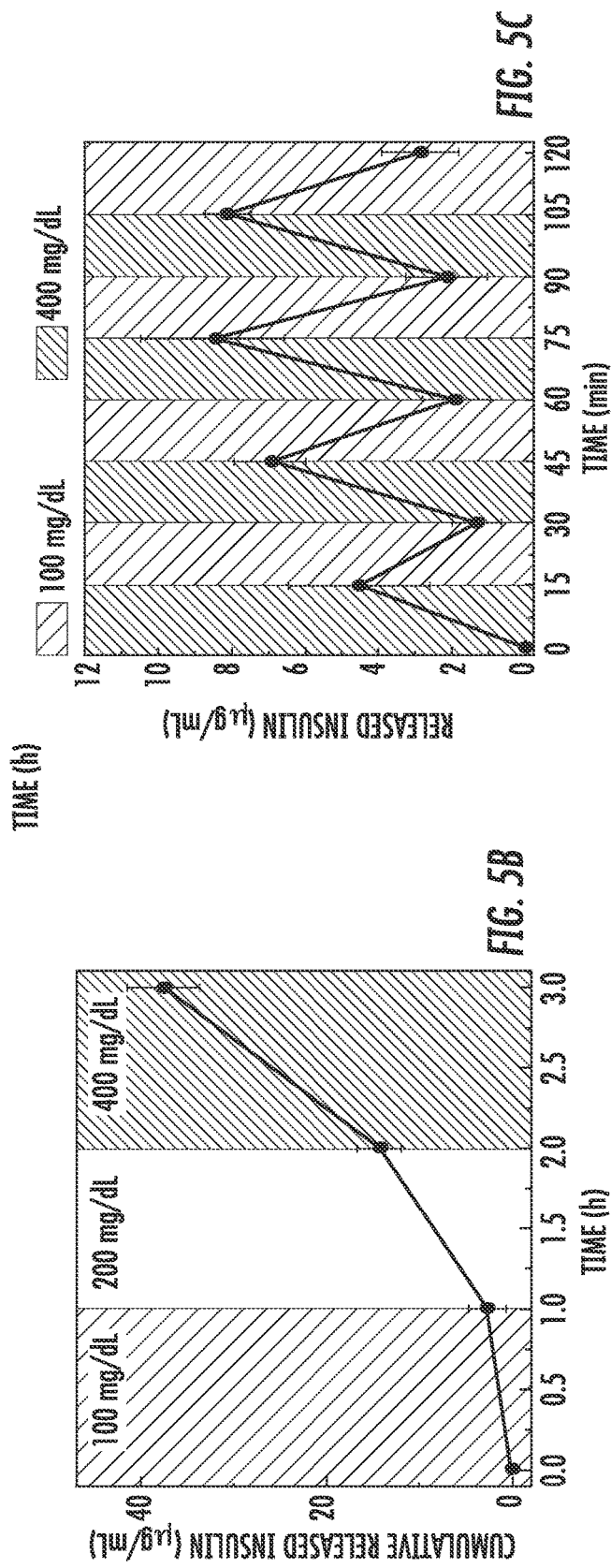

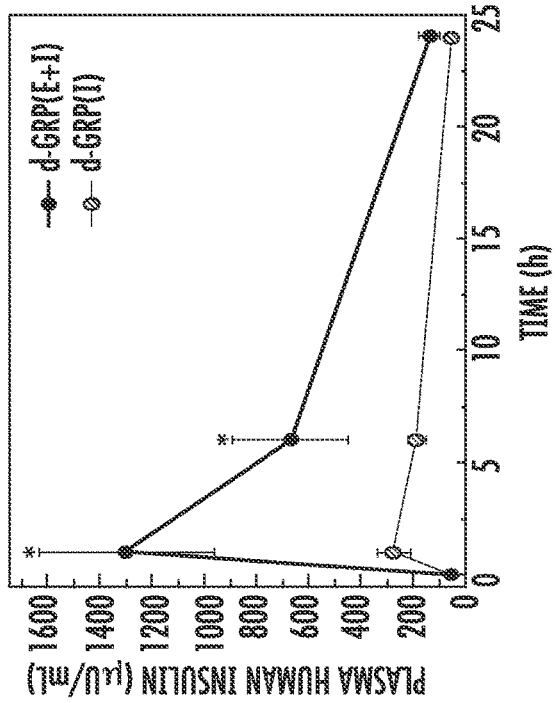
FIG. 6D
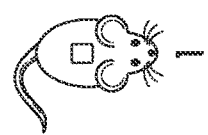 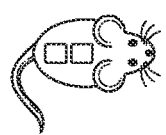
FIG. 6E
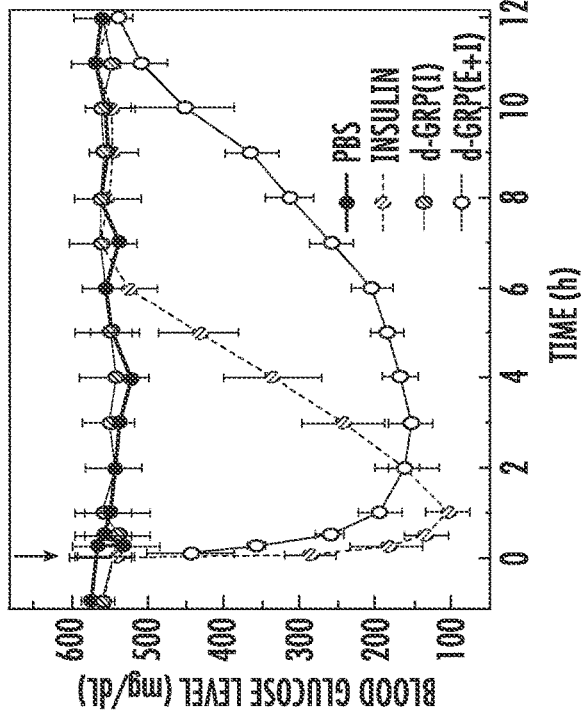 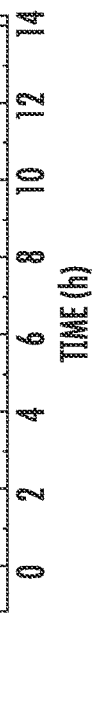
FIG. 6F

PATCH LOADED WITH DUAL-SENSITIVE VESICLES FOR ENHANCED GLUCOSE-RESPONSIVE INSULIN DELIVERY

RELATED APPLICATIONS

This application claims priority to and the benefit of U.S. Provisional Patent Application Ser. No. 62/418,509, filed Nov. 7, 2016; the disclosure of which is incorporated herein by reference in its entirety.

TECHNICAL FIELD

The presently disclosed subject matter relates to systems and compositions, such as vesicles, nanoparticles, microneedles, and microneedle arrays, for the glucose-sensitive delivery of diabetes treatment agents, such as insulin and/or bioactive derivatives thereof. The systems and compositions are also sensitive to hydrogen peroxide and can eliminate excess hydrogen peroxide. The presently disclosed subject matter further relates to methods of preparing the compositions and to methods of delivering diabetes treatment agents to a subject in need thereof.

ABBREVIATIONS

° C.=degrees Celsius
%=percentage
µL=microliter
µm=micrometer or micron
AUC=area under the curve
BGL=blood glucose level
CD=circular dichroism
cm=centimeter
DI=deionized
dL=deciliter
DLS=dynamic light scattering
DMF=dimethylformamide
ELISA=enzyme linked immunosorbent
FESEM=field-emission scanning electron microscope
FITC=fluorescein isothiocyante
GOx=glucose oxidase
GRP=glucose-responsive polymersome
h=hour
HA=hyaluronic acid
$H_2O_2$=hydrogen peroxide
IU=international units
KCl=potassium chloride
kg=kilogram
$KH_2PO_4$=monopotassium phosphate
MBA=N,N'-methylene bisacrylamide
mg=milligram
m-HA=acrylate-modified hyaluoric acid
min=minutes
mL=milliliter
mm=millimeter
mM=millimolar
mmol=millimole
MN=microneedle
N=Newton
NaCl=sodium chloride
NADPH=nicotinamide adenine dinucleotide phosphate
$Na_2HPO_4$=disodium phosphate
NI=2-nitroimidazole
nm=nanometer
NMR=nuclear magnetic resonance
$O_2$=oxygen
PBS=phosphate buffered saline
PEG=poly(ethylene glycol)
s=seconds
SEM=scanning electron microscope
Ser=serine
STZ=streptozotocin
TEM=transmission electron microscope
UV=ultraviolet

BACKGROUND

Diabetes mellitus is a group of metabolic diseases characterized by accumulation of glucose in the blood. See Pickup et al., Diabetes-Metabolism Research and Reviews, 24, 604-610 (2008); and Stumvoll et al., Lancet, 365, 1333-1346 (2005). As of 2014, 387 million people suffer from diabetes worldwide, and the number is estimated to be 592 million by 2035. See Mo et al., Chemical Society Reviews, 43, 3595-3629 (2014); and Tabák et al., Lancet, 379, 2279-2290 (2012). The traditional care for diabetics involves continuous monitoring of blood glucose levels and subsequent insulin injections to maintain normoglycemia. See Owens et al., Lancet, 358, 739-746 (2001). However, such self-administration can be associated with pain and limited glucose control. See Bratlie et al., Advanced Healthcare Materials, 1, 267-284 (2012); and Ravaine et al., Journal of Controlled Release, 132, 2-11 (2008).

Over the past decade, the development of transdermal injection devices with micron-scale needles for insulin delivery has been attempted. See Martanto et al., Pharmaceutical Research 21, 947-952 (2004); Narayan, J. Biomedical Nanotechnology, 10, 2244-2260 (2014); Ling et al., Acta Biomaterialia, 9, 8952-8961 (2013); Prausnitz et al., Nature Biotechnology, 26, 1261-1268 (2008); and Yang et al., Nature Communications, 4, (2013), doi 10.1038/ncomms2715. Yet, there is still a need for additional insulin delivery systems and related compositions, particularly for "closed-loop" delivery systems that can deliver insulin to a subject rapidly in response to changes in blood glucose and with little to no pain or other side effects, such as localized inflammation.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides a composition comprising: (a) an amphiphilic polymeric material comprising a polymer conjugated to a hydrogen peroxide-sensitive hydrophobic group and a hypoxia-sensitive hydrophobic group, wherein said hydrogen peroxide-sensitive group comprises a hydrogen peroxide-sensitive moiety that can be oxidized in the presence of hydrogen peroxide to form a hydrophilic moiety and said hypoxia-sensitive hydrophobic group comprises a hypoxia-sensitive moiety that can be reduced in the presence of a hypoxic environment to form a hydrophilic moiety; (b) an insulin or a bioactive derivative thereof; and (c) a glucose oxidizing agent.

In some embodiments, the polymer is biodegradable. In some embodiments, the polymer comprises a diblock copolymer. In some embodiments, the polymer comprises a polyamino acid, such as polyserine; a poly(ethylene glycol) (PEG); or a combination thereof.

In some embodiments, the hydrogen peroxide-sensitive moiety comprises a thioether. In some embodiments, the hypoxia-sensitive moiety comprises a nitroimidazole. In some embodiments, the hydrogen peroxide-sensitive hydrophobic group and/or the hypoxia-sensitive hydrophobic group is covalently bound to the polymer. In some embodiments, the amphiphilic polymeric material comprises poly(ethylene glycol) (PEG) and polyserine modified with 2-nitroimidazole via a thioether moiety.

In some embodiments, the glucose oxidizing agent is glucose oxidase (GOx). In some embodiments, the insulin is selected from a human insulin, a recombinant human insulin, insulin from a non-human animal, a fast-acting insulin, a rapid-acting insulin analog, an intermediate-acting insulin, and/or a long-acting insulin. In some embodiments, the insulin is recombinant human insulin.

In some embodiments, the amphiphilic polymeric material forms a vesicle encapsulating said insulin or bioactive derivative thereof and said glucose oxidizing agent.

In some embodiments, the presently disclosed subject matter provides a nanoparticle comprising a composition comprising: (a) an amphiphilic polymeric material comprising a polymer conjugated to a hydrogen peroxide-sensitive hydrophobic group and a hypoxia-sensitive hydrophobic group, wherein said hydrogen peroxide-sensitive group comprises a hydrogen peroxide-sensitive moiety that can be oxidized in the presence of hydrogen peroxide to form a hydrophilic moiety and said hypoxia-sensitive hydrophobic group comprises a hypoxia-sensitive moiety that can be reduced in the presence of a hypoxic environment to form a hydrophilic moiety; (b) an insulin or a bioactive derivative thereof; and (c) a glucose oxidizing agent.

In some embodiments, the presently disclosed subject matter provides a vesicle comprising an amphiphilic polymeric material, wherein the amphiphilic polymeric material comprises a polymer conjugated to a hydrogen peroxide-sensitive hydrophobic group and a hypoxia-sensitive hydrophobic group, wherein said hydrogen peroxide-sensitive group comprises a hydrogen peroxide-sensitive moiety that can be oxidized in the presence of hydrogen peroxide to form a hydrophilic moiety and said hypoxia-sensitive hydrophobic group comprises a hypoxia-sensitive moiety that can be reduced in the presence of a hypoxic environment to form a hydrophilic moiety, and further wherein (i) an insulin or a bioactive derivative thereof and (ii) a glucose oxidizing agent are contained within said vesicle.

In some embodiments, the polymer comprises a polyamino acid, such as polyserine; a poly(ethylene glycol) (PEG); or a combination thereof. In some embodiments, the hydrogen peroxide-sensitive moiety comprises a thioether. In some embodiments, the hypoxia-sensitive moiety comprises a nitroimidazole. In some embodiments, the insulin or bioactive derivative thereof is recombinant human insulin. In some embodiments, the glucose oxidizing agent is glucose oxidase (GOx).

In some embodiments, the presently disclosed subject matter provides a microneedle array comprising the presently disclosed vesicles, optionally wherein said microneedle array comprises a plurality of microneedles, wherein each of said plurality of microneedles has a length of between about 20 and about 1000 microns, further optionally wherein each of the plurality of microneedles has a length of about 600 microns. In some embodiments, the microneedle array is provided as part of a skin patch, optionally wherein said patch comprises one or more backing layers and/or skin-compatible adhesives.

In some embodiments, the presently disclosed subject matter provides a closed-loop insulin delivery system comprising a microneedle array comprising the presently disclosed vesicles.

In some embodiments, the presently disclosed subject matter provides a method of delivering an insulin or a bioactive insulin derivative to a subject in need thereof, the method comprising providing a microneedle array comprising the presently disclosed vesicles, and applying said array to a skin surface of said subject, wherein when glucose comes into contact with the microneedle array, it is oxidized, thereby (1) creating a hypoxic environment that results in the reduction of the hypoxia-sensitive moiety to form a hydrophilic moiety, and (2) producing hydrogen peroxide that results in the oxidation of the hydrogen peroxide-sensitive moiety to form a hydrophilic moiety, leading to disruption of vesicles and release of an insulin or a bioactive insulin derivative contained in the vesicles. In some embodiments, the delivery of the insulin or bioactive insulin derivative is at a rate corresponding to the glucose concentration coming into contact with the microneedle array.

In some embodiments, the subject is a mammal. In some embodiments, the subject is diabetic.

In some embodiments, the presently disclosed subject matter provides a method of preparing a microneedle array for the glucose-sensitive delivery of insulin or a bioactive derivative thereof, the method comprising: (a) preparing an aqueous solution of a vesicle comprising an amphiphilic polymeric material, wherein the amphiphilic polymeric material comprises a polymer conjugated to a hydrogen peroxide-sensitive hydrophobic group and a hypoxia-sensitive hydrophobic group, wherein said hydrogen peroxide-sensitive group comprises a hydrogen peroxide-sensitive moiety that can be oxidized in the presence of hydrogen peroxide to form a hydrophilic moiety and said hypoxia-sensitive hydrophobic group comprises a hypoxia-sensitive moiety that can be reduced in the presence of a hypoxic environment to form a hydrophilic moiety, and further wherein (i) an insulin or a bioactive derivative thereof and (ii) a glucose oxidizing agent are contained within said vesicle; (b) dispersing said aqueous solution into a mold comprising a plurality of microneedle cavities, thereby providing a filled mold; (c) drying the filled mold to remove water; and (d) removing the mold to provide a microneedle array.

In some embodiments, the method further comprises cross-linking polymeric materials in the microneedle array. In some embodiments, step (b) is performed under vacuum. In some embodiments, after step (b), the mold is centrifuged to compact the vesicles into the microneedle cavities. In some embodiments, step (c) is performed in a vacuum desiccator. In some embodiments, the mold comprises silicone. In some embodiments, the cross-linking is performed by exposure to UV irradiation.

Accordingly, it is an object of the presently disclosed subject matter to provide glucose-sensitive compositions (e.g., nanoparticles, vesicles, and/or microneedle arrays) comprising an amphiphilic polymer that comprises a hydrogen peroxide-sensitive moiety, a hypoxia-sensitive moiety, an insulin or a bioactive derivative thereof, and a glucose oxidizing agent, as well as methods of preparing and using said compositions.

An object of the presently disclosed subject matter having been stated hereinabove, and which is achieved in whole or in part by the presently disclosed subject matter, other objects will become evident as the description proceeds when taken in connection with the accompanying drawings and examples as best described herein below.

BRIEF DESCRIPTION OF THE DRAWINGS

FIG. 3A is a series of transmission electron microscopy (TEM) micrograph images of dual-sensitive glucose-responsive polymersomes (d-GRPs) encapsulating insulin and glucose oxidase enzyme prior to incubation with 400 milligrams per deciliter (mg/dL) glucose (left), or after incubation with 400 mg/dL glucose for 20 minutes (min) (second from left), for 1 hour (second from right), or 24 hours (right). The scale bars in the bottom right of the images represent 100 nanometers (nm).

FIG. 3B is a graph showing the size distribution (diameter in nanometers (nm)) of dual-sensitive glucose-responsive polymersomes (d-GRPs) encapsulating insulin and glucose oxidase enzyme prior to incubation with glucose.

FIG. 3C is a graph showing the size distribution (diameter in nanometers (nm)) of dual-sensitive glucose-responsive polymersomes (d-GRPs) encapsulating insulin and glucose oxidase enzyme after incubation with glucose (400 milligrams per deciliter) for 24 hours.

FIG. 3D is a 2.5 dimensional fluorescence image of fluorescein isothiocyante (FITC)-insulin-loaded dual-sensitive glucose-responsive polymersomes (d-GRPs) prior to incubation with glucose.

FIG. 3E is a 2.5 dimensional fluorescence image of fluorescein isothiocyante (FITC)-insulin-loaded dual-sensitive glucose-responsive polymersomes (d-GRPs) after incubation with glucose (400 milligrams per deciliter) for 24 hours at 37 degrees Celsius.

FIG. 3F is a graph showing the sensitivity of dual-sensitive glucose-responsive polymersomes (d-GRPs; bars with wide stripes running from top right to bottom left) and non-hydrogen peroxide sensitive glucose-responsive polymersomes (GRPs; bars with narrow stripes running form top left to bottom right) to hydrogen peroxide as assessed by a fluorometric hydrogen peroxide assay kit. Student's t-test: *$p<0.05$, ***$p<0.001$.

FIG. 5A is graph showing in vitro accumulated insulin release from dual-sensitive glucose-responsive polymersomes (d-GRPs) incubated in different glucose solutions of various glucose concentration (0 milligram per deciliter (mg/dL) glucose (PBS, filled circles); 100 mg/dL glucose (striped circles); and 400 mg/dL glucose (open circles) at 37 degrees Celsius.

FIG. 5B is a graph showing self-regulated profiles of dual-sensitive glucose-responsive polymersomes (d-GRPs) containing glucose oxidase (GOx) and insulin. The rate of insulin release is shown as a function of glucose concentration (i.e., 100 milligrams per deciliter (mg/dL) (left, wide stripes), 200 mg/dL (middle, no stripes), or 400 mg/dL (right, narrow stripes)).

FIG. 5C is a pulsatile release profile of dual-sensitive glucose-responsive polymersomes (d-GRPs) exposed sequentially to a 100 milligram per deciliter (mg/dL) glucose solution (sections with wide stripes) for ten minutes and then a 400 mg/dL glucose solution (sections with narrow stripes) for ten minutes for several repetitions.

FIG. 6D is a graph of blood glucose levels during in vivo studies of a dual-sensitive, glucose-responsive polymersomes (d-GRP)-loaded microneedle (MN)-array patch treatment for type I diabetes in streptozotocin (STZ)-induced diabetic mice. Data is provided for mice treated with blank MN (MN not containing insulin or an enzyme, PBS, filled circles with heavy solid line); MN loaded with human recombinant insulin (Insulin, striped circles with dotted line), MN loaded with d-GRPs containing human recombinant insulin only (d-GRP(I), striped circles with solid line); and MN loaded with d-GRPs containing insulin and glucose oxidase enzyme (d-GRP(E+I), open circles with solid line).

FIG. 6E is a graph of plasma insulin concentrations during in vivo studies of a dual-sensitive, glucose-responsive polymersomes (d-GRP)-loaded microneedle (MN)-array patch treatment for type I diabetes in streptozotocin (STZ)-induced diabetic mice. Data is provided for mice treated with MN loaded with d-GRPs containing human recombinant insulin only (d-GRP(I), striped circles) and MN loaded with d-GRPs containing insulin and glucose oxidase enzyme (d-GRP(E+I), filled circles). $*p<0.05$ for administration with d-GRP(E+I)-loaded MNs compared with administration of d-GRP(I).

FIG. 6F is a graph showing blood glucose changes in mice treated with additional administration of a microneedle (MN) array patch one hour post administration of a first dual-sensitive glucose-responsive polymersome (d-GRP)-loaded MN array patch, where the first d-GRP-loaded MN array patch contained d-GRPs loaded with insulin and glucose oxidase enzyme (i.e., d-GRP(E+I)). The additional MN array patch contained d-GRPs loaded with both insulin and glucose oxidase enzyme (d-GRP(E+I)+d-GRP(E+I), striped circles); d-GRPs loaded with insulin (d-GRP(E+I)+(d-GRP(I), filled circles); or MNs loaded with insulin only (GRP(E+I)+Insulin, open circles). The black arrows indicate the administration time points of the first (1) and second (2) MN array patch.

DETAILED DESCRIPTION

Figure 1A:
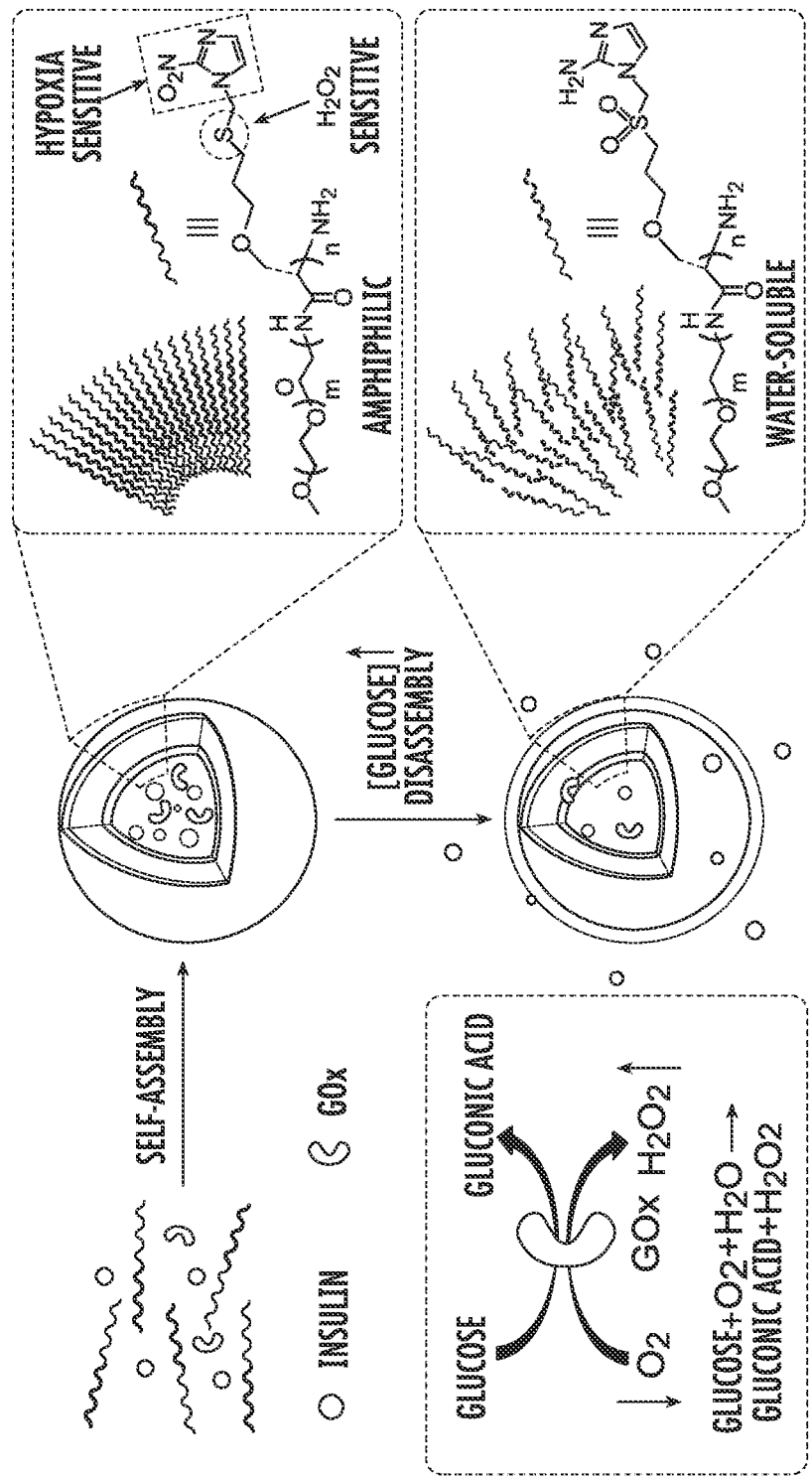
FIG. 1A is a schematic drawing showing the formation and subsequent disassembly of a glucose-responsive delivery system comprising hypoxia and hydrogen peroxide ($H_2O_2$) dual-sensitive glucose-responsive polymersomes (d-GRPs). The d-GRPs are prepared using hypoxia sensitive and $H_2O_2$ sensitive amphiphilic polymers and are loaded with insulin and a glucose oxidizing enzyme, i.e., glucose oxidase (GOx). The reduction of the hydrophobic hypoxia-sensitive moiety, i.e., 2-nitroimidazole (NI), in the d-GRPs to form hydrophilic moieties (2-aminoimidazole) triggered by hypoxia caused by GOx oxidation of glucose and the oxidation of the $H_2O_2$-sensitive moiety, i.e., a thioether, to form a hydrophilic group (i.e., a sulfone) triggered by the increase in the $H_2O_2$ side-product of the GOx oxidation of glucose, results in transforming the amphiphilic polymer into a hydrophilic polymer, causing the d-GRPs to disassemble and release insulin.

The presently disclosed subject matter will now be described more fully hereinafter with reference to the accompanying Examples and Drawings, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a composition" or "a polymer" includes a plurality of such compositions or polymers, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, nitro, amino, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "aralkyl" refers to an -alkyl-aryl group, optionally wherein the alkyl and/or aryl group comprises one or more alkyl or aryl group substituents.

In some embodiments, the term "bivalent" refers to a group that can bond (e.g., covalently bond) or is bonded to two other groups, such as other alkyl, aralkyl, cycloalkyl, or aryl groups. Typically, two different sites on the bivalent group (e.g., two different atoms) can bond to groups on other molecules. For example, the bivalent group can be an alkylene group.

"Alkylene" can refer to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

"Arylene" refers to a bivalent aryl group.

The term "amino" refers to the —NR'R" group, wherein R' and R" are each independently selected from the group including H and substituted and unsubstituted alkyl, cycloalkyl, heterocycle, aralkyl, aryl, and heteroaryl. In some embodiments, the amino group is —$NH_2$. "Aminoalkyl" and "aminoaryl" refer to the —NR'R" group, wherein R' is as defined hereinabove for amino and R" is substituted or unsubstituted alkyl or aryl, respectively.

The terms "carboxylate" and "carboxylic acid" can refer to the groups —C(=O)O$^-$ and —C(=O)OH, respectively. In some embodiments, "carboxylate" can refer to either the —C(=O)O$^-$ or —C(=O)OH group.

The term "thioether" refers to a R—S—R' group, wherein R and R' are each independently selected from the group including substituted and unsubstituted alkyl, cycloalkyl, heterocycle, aralkyl, aryl and heteroaryl.

The term "sulfone" as used herein refers to the R—S(=O)$_2$—R' group, wherein R and R' are each independently selected from the group including substituted and unsubstituted alkyl, cycloalkyl, heterocycle, aralkyl, aryl and heteroaryl.

The terms "nanoscale," "nanomaterial," "nanometer-scale polymer" "nanocluster", "nanoparticle", and other grammatical variations thereof refer to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is less than about 10 nm.

In some embodiments, the nanoparticle is approximately spherical. When the nanoparticle is approximately spherical, the characteristic dimension can correspond to the diameter of the sphere. In addition to spherical shapes, the nanoparticle or other nanoscale material can be disc-shaped, oblong, polyhedral, rod-shaped, cubic, or irregularly-shaped. A nanoscale material can also comprise clusters of sphere-, oblong-, polyhedral-, rod-, disc-, cube- or irregularly-shaped particles or combinations of different shaped particles.

The term "micro" (e.g., in "microneedle") as used herein refers to a structure having at least one region with a dimension of less than about 1,000 microns (μm). In some embodiments, the term "micro" refers to a structure having a dimension between about 1 micron and about 1,000 microns.

The term "diameter" is art-recognized and is used herein to refer to either the physical diameter or the hydrodynamic diameter. The diameter of an essentially spherical particle can refer to the physical or hydrodynamic diameter. As used herein, the diameter of a non-spherical particle can refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering.

"Monodisperse" is used herein to describe a population of particles where all of the particles are the same or nearly the same size. For example, "monodisperse" can refer to particle distributions in which 90% of the distribution lies within 15%, 10% or 5% of the median particle size.

The terms "polymer" and "polymeric" refer to chemical structures that have repeating units (i.e., multiple copies of a given chemical substructure). As used herein, polymers can refer to groups having more than 10 repeating units and/or to groups wherein the repeating unit is other than methylene. Polymers can be formed from polymerizable monomers. A polymerizable monomer is a molecule that comprises one or more reactive moieties {e.g., siloxy ethers, hydroxyls, amines, vinylic groups (i.e., carbon-carbon double bonds), halides (i.e., C, Br, F, and I), esters, activated esters, and the like} that can react to form bonds with other molecules. Generally, each polymerizable monomer molecule can bond to two or more other molecules. In some cases, a polymerizable monomer will bond to only one other molecule, forming a terminus of the polymeric material. Some polymers contain biodegradable linkages, such as esters or amides, such that they can degrade overtime under biological conditions.

A "copolymer" refers to a polymer derived from more than one species of monomer.

As used herein, a "block copolymer" refers to a copolymer that comprises blocks (i.e., polymeric sub-sections of the whole copolymer) in a linear sequence. A "block" refers to a portion of a copolymer that has at least one feature that is not present in the adjacent portions of the macromolecule. Thus, a "block copolymer" can refer to a copolymer in which adjacent blocks are constitutionally different, i.e., each of these blocks comprises constitutional units derived from different characteristic species of monomer or with different composition or sequence distribution of constitutional units.

For example, a diblock copolymer of PEG and polyserine can be referred to as PEG-block-polyserine. Such a copolymer can also be referred to generically as an "AB block copolymer." Likewise, a triblock copolymer can be represented as "ABA." Other types of block polymers exist, such as multiblock copolymers of the $(AB)_n$ type, ABC block polymers comprising three different blocks, and star block polymers, which have a central point with three or more arms, each of which is in the form of a block copolymer, usually of the AB type.

Polydispersity (PDI) refers to the ratio ($M_w/M_n$) of a polymer sample. $M_w$ refers to the mass average molar mass (also commonly referred to as weight average molecular weight). $M_n$ refers number average molar mass (also commonly referred to as number average molecular weight).

"Biocompatible" as used herein, generally refers to a material and any metabolites or degradation products thereof that are generally non-toxic to the recipient and do not cause any significant adverse effects to the recipient.

"Biodegradable" as used herein, generally refers to a material that will degrade or erode under physiologic conditions to smaller units or chemical species that are capable of being metabolized, eliminated, or excreted by the subject. In some embodiments, the degradation time is a function of polymer composition and morphology. Suitable degradation times are from days to weeks. For example, in some embodiments, the polymer can degrade over a time period from seven days to 24 weeks, optionally seven days to twelve weeks, optionally from seven days to six weeks, or further optionally from seven days to three weeks.

The term "hydrophilic" can refer to a group that dissolves or preferentially dissolves in water and/or aqueous solutions.

The term "hydrophobic" refers to groups that do not significantly dissolve in water and/or aqueous solutions and/or which preferentially dissolves in fats and/or non-aqueous solutions.

The term "amphiphilic" refers to a molecule or polymer that contains both hydrophilic and hydrophobic groups.

The terms "conjugate" and "conjugated" can refer to compositions that comprise at least two different chemical moieties or molecules (e.g., small molecules, polymers, proteins, etc.) bonded to one another, such as via ionic, coordinative or covalent bonds. In some embodiments, the term "conjugate" refers to moieties or molecules that are covalently bonded to one another. In some embodiments, the conjugate can comprise two different chemical moieties associated with one another via intermolecular forces such as hydrogen bonding, London dispersion forces, van der Waals' interactions, etc.

The term "insulin" as used herein refers to insulin from a human or other mammal. In some embodiments, the term "insulin" refers to human insulin. In some embodiments, the term "insulin" refers to recombinant human insulin.

"Bioactive derivative" as used herein refers to human insulin or another mammalian insulin in which one or more amino acid residues have been replaced by another amino acid residue or deleted, in which the A chain and/or the B chain has been extended by addition of one or more amino acid residues at the N-terminal or at the C-terminal, and/or in which the insulin has been modified by the addition of one or more chemical substituents. The derivative can function to replace endogenous insulin and retains at least some of the biological activity of endogenous insulin. Insulin derivatives can have different pharmacokinetics than endogenous insulin. Dosages can be optimized based on the pharmacokinetics of the insulin derivative relative to human insulin based on known pharmacokinetics by one of skill in the art.

The term "diabetes treatment agent" as used herein can refer to a therapeutic agent that treats diabetes or a complication thereof (such as, but not limited to, diabetic neuropathy, diabetic retinopathy, diabetic nephropathy, glaucoma, and diabetic ketoacidosis) or another glucose metabolism disorder that results in hyperglycemia. In some embodiments, the diabetes treatment agent is an insulin or a bioactive derivative thereof or a non-insulin-based treatment agent known in the art for use in the treatment of diabetes. Suitable non-insulin-based treatment agents for use in the treatment of diabetes include, but are not limited to, insulin sensitizers, DPP IV inhibitors, glucagon-like peptide 1 (GLP-1) and analogs thereof, insulin secretagogues, such as, but not limited to sulfonylureas, meglitinides, gastric inhibitory polypeptide (GIP), insulin receptor activators, biguanides, thiazolidinediones, alpha-glucosidase inhibitors, and the like. In some embodiments, the diabetes treatment agent is an insulin or a bioactive derivative.

The terms "cross-linking reagent" or "cross-linking agent" refer to a compound that includes at least two reactive functional groups (or groups that can be deblocked or deprotected to provide reactive functional groups), which can be the same or different. In some embodiments, the two reactive functional groups can have different chemical reactivity (e.g., the two reactive functional groups are reactive (e.g., form bonds, such as covalent bonds) with different types of functional groups on other molecules, or one of the two reactive functional groups tends to react more quickly with a particular functional group on another molecule than the other reactive functional group). Thus, the cross-linking reagent can be used to link (e.g., covalently bond) two other entities (e.g., molecules, polymers, proteins, nucleic acids, vesicles, liposomes, nanoparticles, microparticles, etc.) to form a cross-linked composition.

The term "vesicle" can refer to an artificially created particle, (in some embodiments, a nanoparticle) comprising fluid enclosed by a concentric layer or layers of a molecule or polymer (e.g., an amphiphilic polymer). When the vesicle comprises a concentric layer or layers of a polymer, the vesicle can also be referred to as a "polymersome." Dissolved or suspended in the fluid can be one or more therapeutic agents (e.g., small molecules, proteins, nucleic acids, etc.). According to some embodiments of the presently disclosed subject matter, the fluid can comprise an insulin or bioactive derivative thereof, and a glucose oxidizing agent, such as glucose oxidase dissolved in an aqueous solution. The fluid can also comprise an additional therapeutic agent, e.g., in addition to the insulin or bioactive derivative thereof, such as another therapeutic agent for treating diabetes or a complication thereof. In some embodiments, the additional therapeutic agent can be a water-soluble therapeutic agent.

The term "hyperglycemia", as used herein, can refer to a condition in which an elevated amount of glucose circulates in the blood plasma of a subject relative to a healthy individual. Hyperglycemia can be diagnosed using methods known in the art, including measurement of fasting blood glucose levels.

The term "hyperinsulinemia", as used herein, can refer to a condition in which there are elevated levels of circulating insulin when, concomitantly, blood glucose levels are either elevated or normal. Hyperinsulinemia can be caused by insulin resistance associated with dyslipidemia, such as high triglycerides, high cholesterol, high low-density lipoprotein (LDL) and low high-density lipoprotein (HDL); high uric acids levels; polycystic ovary syndrome; type II diabetes and obesity.

The term "insulin resistance" as used herein can refer to a condition where a normal amount of insulin is unable to produce a normal physiological or molecular response. In some cases, a hyper-physiological amount of insulin, either endogenously produced or exogenously administered, is able to overcome the insulin resistance, in whole or in part, and produce a biologic response.

The term "metabolic syndrome" as used herein can refer to an associated cluster of traits that includes, but is not limited to, hyperinsulinemia, abnormal glucose tolerance, obesity, redistribution of fat to the abdominal or upper body compartment, hypertension, dysfibrinolysis, and dyslipidemia characterized by high triglycerides, low high density lipoprotein (HDL)-cholesterol, and high small dense low density lipoprotein (LDL) particles. Subjects having metabolic syndrome are at risk for development of Type 2 diabetes and/or other disorders (e.g., atherosclerosis).

The term "glucose tolerance," as used herein, can refer to the ability of a subject to control the level of plasma glucose and/or plasma insulin when glucose intake fluctuates. For example, glucose tolerance encompasses the ability to reduce the level of plasma glucose back to a level before the intake of glucose within about 120 minutes or so.

II. General Considerations

Diabetes mellitus is a chronic disease associated with elevated glucose in the blood, which currently affects 415 million people worldwide. See Mo et al., Chem. Soc., Rev., 2014, 43(10), 3595-3629; and Veiseh et al., Nat. Rev. Drug Discov., 2015, 14(1), 45-57. Insulin, a hormone to help cells take in glucose for energy, is essential for the treatment of type 1 and advanced type 2 diabetic patients in order to maintain normoglycemia. See Owens et al., Lancet, 2001, 358(9283), 739-746. However, the traditional exogenous insulin injection does not closely match the physiological release of insulin, often resulting in inadequate glycemic control (see Veiseh et al., Nat. Rev. Drug Discov., 2015, 14(1), 45-57; and Bratlie et al., Adv. Healthcare. Mater., 2012, 1(3), 267-284) and subsequent consequences such as limb amputation, blindness and kidney failure. In addition, overtreatment with insulin may lead to hypoglycemia, which can cause behavioral and cognitive disturbance, seizures, loss of consciousness, brain damage, and even death. See Ohkubo et al., Diabetes Res. Clin. Pract., 1995, 28(2), 103-117. A "smart" or closed-loop glucose-responsive insulin delivery system that can mimic the β-cells to "secrete" insulin in response to a high blood glucose level (BGL) is desirable to regulate glycemia with minimal effort and to improve the health and quality of life for diabetic patients. See Mo et al., Chem. Soc., Rev., 2014, 43(10), 3595-3629; Veiseh et al., Nat. Rev. Drug Discov., 2015, 14(1), 45-57; Wu et al., Chem. Rev., 2011, 111(12), 7855-7875; and Gilroy et al., J. Controlled Release, 2015; dx.doi.org/10.1016/jconrel.2015.12.002.

In order to achieve this goal, closed-loop systems usually contain a glucose monitoring module and an insulin releasing module. See Mo et al., Chem. Soc., Rev., 2014, 43(10), 3595-3629; and Veiseh et al., Nat. Rev. Drug Discov., 2015, 14(1), 45-57. For instance, the current closed-loop electromechanical systems include a continuous glucose sensor and an external insulin infusion pump. See Veiseh et al., Nat. Rev. Drug Discov., 2015, 14(1), 45-57. However, there are still some challenges that limit the application of these systems, such as lag in blood glucose feedback and biofouling. See Pickup New Engl. J. Med., 2012, 366(17), 1616-1624.

As an alternative, chemically controlled glucose-responsive systems have also been investigated during the last few decades. See Mo et al., Chem. Soc., Rev., 2014, 43(10), 3595-3629; Veiseh et al., Nat. Rev. Drug Discov., 2015, 14(1), 45-57; and Gilroy et al., J. Controlled Release, 2015; dx.doi.org/10.1016/jconrel.2015.12.002. Typically, an insulin embedded matrix with glucose-responsive elements can adjust the insulin release rate through structural changes such as swelling, shrinking, degradation, or dissociation in response to ambient glucose levels. See Gordijo et al., Adv. Funct. Mater., 2011, 21(1), 73-82; Gu et al., ACS Nano, 2013, 7(8), 6758-6766; and Gu et al., ACS Nano, 7(5), 4194-4201. Possible glucose-responsive elements for these systems include glucose oxidase (GOx) (see Gu et al., ACS Nano, 2013, 7(8), 6758-6766; Gu et al., ACS Nano, 7(5), 4194-4201; Fischel-Ghodsian et al., Proc. Natl. Acad. Sci. USA, 1988, 85(7), 2403-2406; and Kang et al., J. Controlled Release, 2003, 86(1), 115-121), phenylboronic acid (PBA) (see Katoaka et al., J. Am. Chem. Soc., 1998, 120(48), 12694-12695; and Chou et al., Proc. Natl. Acad. Sci. USA, 2015, 112(8), 2401-2406) and glucose-binding protein (GBP). See Makino et al., J. Controlled Release, 1990, 12(3), 235-239; Podual et al., Polymer, 2000, 41(11), 3975-3983; and Podual et al., J. Controlled Release, 2000, 67(1), 9-17. In spite of these available chemistries, few synthetic glucose-responsive systems show promise in vivo. Challenges remain to demonstrate a system having fast responsiveness with kinetics similar to a healthy pancreas, biocompatibility without long-term side effects, and ease of administration.

GOx is an enzyme which can convert glucose to gluconic acid in the presence of oxygen:

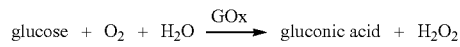

See Wu et al., Chem. Rev., 111(12):7855-7875 (2011). Glucose-responsive systems employing GOx have previously been integrated with pH-sensitive materials, which can either be protonated or degraded with a local decrease of pH, promoted by increasing glucose concentration. See Gu et al., ACS Nano, 2013, 7(8), 6758-6766; Gu et al., ACS Nano, 2013, 7(5), 4194-4201; Podual et al., J. Controlled Release, 2000, 67(1), 9-17; and Tai et al., Biomacromolecules, 2014, 15(10), 3495-3502. Yet, such pH decrease-dependent methods can be compromised by slow responsiveness, especially in a buffered physiologic environment. See Veiseh et al., Nature Reviews Drug Discovery, 14(1): 45-57 (2015). Recently, a hypoxia-sensitive mechanism for achieving fast, glucose-responsive, insulin delivery has been reported. See Yu et al., Proc. Natl. Acad. Sci. USA, 2015, 112(27), 8260-8265 and WO 2016/172320, the disclosure of which is incorporated herein by reference in its entirety.

According to an aspect of the presently disclosed subject matter, a hypoxia and $H_2O_2$ dual-sensitive diblock copolymer is provided. In some embodiments, the copolymer can include poly(ethylene glycol) (PEG) and polyserine blocks, wherein the polyserine blocks are modified with 2-nitroimidazole via a thioether moiety. The structure of this representative copolymer, designated PEG-Poly(Ser-S-NI), is shown as compound 10 in FIG. 2A). The thioether serves as a $H_2O_2$-sensitive moiety that can turn the polymer more hydrophilic when it is converted into a sulfone by $H_2O_2$. See Napoli et al., Nat. Mater., 2004, 3(3), 183-189; and Huo et al., Polym. Chem., 2014, 5(5), 1519-1528. This amphiphilic copolymer can self-assemble into a nano-scale bilayer vesicle structure (i.e., a "polymersome"), which can encapsulate recombinant human insulin and GOx in its aqueous core. When exposed to a high blood glucose level, the glucose can diffuse across the polymeric bilayer membrane and interact with GOx. See FIG. 1A. During the glucose oxidation process catalyzed by GOx, dissolved oxygen can be rapidly consumed. The resulting local hypoxic environment can promote the bioreduction of NI groups in the copolymer into hydrophilic 2-aminoimidazoles. The bioreduction can be catalyzed by a series of nitroreducatases. See Yu et al., Proc. Natl. Acad. Sci. USA, 2015, 112(27), 8260-8265; Nunn et al., Eur. J. Nucl. Med., 1995, 22(3), 265-280; and Krohn et al., J. Nucl. Med., 2008, 49(Suppl 2), 129S-148S.

During the enzymatic oxidation of glucose, the undesirable byproduct $H_2O_2$ is also generated, which can lead to free radical-induced damage to skin tissue during the long-term usage of the delivery system and can also reduce the activity of GOx, decreasing the response rate of the delivery system. See Kohen, Biomed., Pharmacother., 1999, 53(4), 181-192; Liu et al., Nat. Nanotechnol., 2013, 8(3), 187-192; Traitel et al., Biomaterials, 2000, 21(16), 1679-1687; and Zhang et al., J. Controlled Release, 2002, 80(1), 169-178. Generally, catalase (CAT) has been incorporated with GOx-based glucose-responsive systems to scavenge $H_2O_2$. See Beers et al., J. Biol. Chem., 1952, 195(1), 133-140. However, oxygen can regenerate during the decomposition of $H_2O_2$ catalyzed by CAT, reducing the hypoxic level and leading to a low release rate. The $H_2O_2$-sensitive thioether moiety in the compositions of the presently disclosed subject matter (e.g., in PEG-Poly(Ser-S-NI)) has the capability of effectively eliminating undesirable $H_2O_2$ to assist GOx's catalysis. Meanwhile, the resulting sulfone groups can convert the polymer to a more water-soluble form. This change in chemical structure can promote the dissociation of the dual-sensitive, glucose-responsive polymersomes (d-GRPs) and the subsequent release of the encapsulated insulin.

Figure 1B:
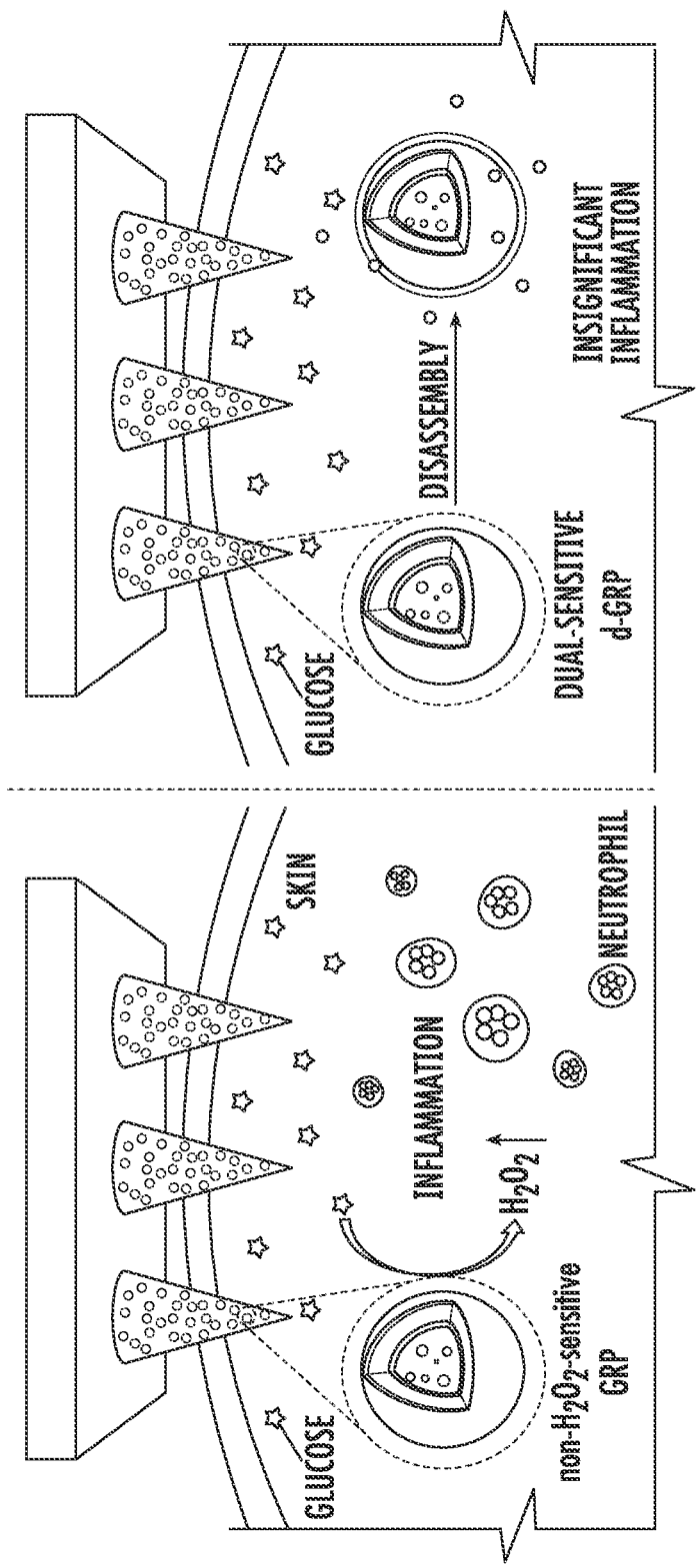
FIG. 1B shows schematic drawings of (left) a non-hydrogen peroxide ($H_2O_2$) sensitive glucose-responsive polymersomes (GRPs)-containing microneedle array skin patch and (right) a hypoxia and hydrogen peroxide dual-sensitive glucose-responsive polymersomes (d-GRPs)-containing microneedle array skin patch for in vivo insulin delivery triggered by a hyperglycemic state. Local inflammation is induced by the GRPs, while the d-GRP-loaded microneedle skin patch can release insulin when triggered by a hyperglycemic state without long-term side effects.
Figure 8:
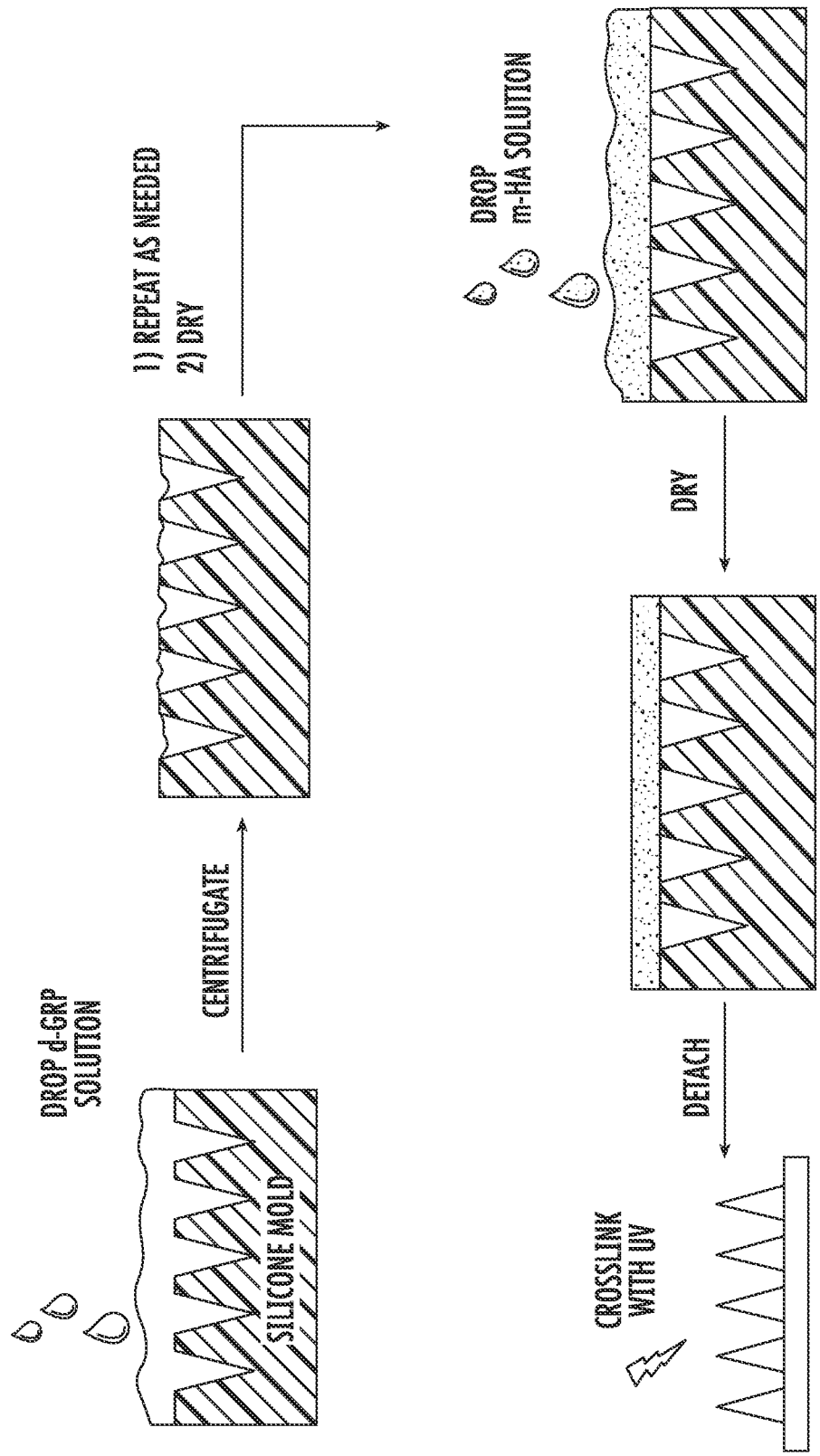
FIG. 8 is a schematic drawing of an exemplary process for preparing dual-sensitive glucose-responsive polymersome (d-GRP)-loaded microneedle (MN) array patches of the presently disclosed subject matter using a silicone mold.

To increase ease of administration, the presently disclosed d-GRPs can be loaded into a microneedle (MN) array-based patch for painless delivery of a diabetes treatment agent (e.g., insulin). See FIGS. 1B and 8. For instance, as shown in FIG. 8, a matrix of microneedles can be made from crosslinked HA, where the cross-linking can improve the stiffness of microneedles and restrict loss of GRPs from needles. As shown in FIG. 1B, right-hand side, upon subcutaneous administration, the d-GRPs loaded in the microneedles disassemble when exposed to a high interstitial fluid glucose level in vascular and lymph capillary networks, thereby promoting the release of the diabetes treatment agent (e.g., insulin) which can be taken up through the regional lymph and capillaries vessels quickly. Furthermore, unlike non-$H_2O_2$-sensitive GRP-loaded MNs (see FIG. 1B, left-hand side), which can cause local inflammation due to the rapid accumulation of $H_2O_2$, the presently disclosed "smart insulin patch" (SIP) with a hypoxia and $H_2O_2$ dual-sensitive mechanism can display tight glucose regulation and prevent long-term disease morbidity without inflammation.

The presently disclosed subject matter relates, in some embodiments, to compositions for the delivery of insulin (or bioactive derivatives thereof) to a subject in need thereof, e.g., for the control of diabetes or another glucose metabolism disorder that leads to hyperglycemia. It could also be useful for delivering anticancer/anti-inflammation drugs and/or other drugs (such as a diabetes treatment agent as disclosed herein) to treat diabetes and/or hyperglycemia and/or the side effects thereof.

In some embodiments, the presently disclosed compositions can provide glucose-sensitive closed-loop insulin delivery to a subject in need thereof, thereby providing for more cost-effective and easier control of diabetes, as well as for the prevention of hypoglycemic complications of the treatment of diabetes.

In some embodiments, the presently disclosed subject matter provides a composition comprising:
(a) an amphiphilic polymeric material comprises a polymer conjugated to a hydrogen peroxide-sensitive hydrophobic group and a hypoxia-sensitive hydrophobic group, wherein said hydrogen peroxide-sensitive group comprises a hydrogen peroxide-sensitive moiety that can be oxidized in the presence of a hydrogen peroxide to form a hydrophilic moiety and said hypoxia-sensitive hydrophobic group comprises a hypoxia-sensitive moiety that can be reduced in the presence of a hypoxic environment to form a hydrophilic moiety;
(b) an insulin or a bioactive derivative thereof; and
(c) a glucose oxidizing agent.

The polymer can be a hydrophilic polymer. The hydrophilic polymer can be a synthetic or a naturally-occurring biocompatible polymer. Suitable hydrophilic polymers can include polar or charged side chain moieties. In some embodiments, the polymer can be biodegradable. In some embodiments, the polymer comprises a diblock copolymer. In some embodiments, the polymer comprises a polyamino acid, such as polyserine; a a poly(ethylene glycol)(PEG); or a combination thereof.

The hydrogen peroxide-sensitive moiety can be any moiety that can undergo a reaction or other structural change in response to contact with $H_2O_2$ (e.g., in a solvent or physiological environment in contact with the amphiphilic polymeric material). For instance, the hydrogen peroxide-sensitive moiety can be a relatively hydrophobic moiety that can undergo an oxidation reaction in response to an increase in $H_2O_2$. The increase in $H_2O_2$ can be the result of a localized increase in $H_2O_2$ concentration caused by enzymatic activity (e.g., of glucose oxidase) that produces $H_2O_2$ as a product (e.g., a side product). In some embodiments, the increase in $H_2O_2$ is a side effect of an increase in glucose concentration near the amphiphilic polymeric material and its subsequent reduction by an enzyme associated with the amphiphilic polymeric material. The product of the interaction of the hydrogen peroxide sensitive moiety with $H_2O_2$ can be hydrophilic or more hydrophilic than the hydrogen peroxide sensitive moiety.

In some embodiments, the hydrogen peroxide-sensitive hydrophobic moiety comprises a thioether. In some embodiments, the hydrogen peroxide-sensitive hydrophobic group is covalently bound to the polymer. In some embodiments, the hydrogen peroxide-sensitive group is bound to both the polymer and the hypoxia-sensitive moiety (e.g., the hydrogen peroxide-sensitive moiety can be part of a bivalent linker linking the hypoxia-sensitive group to the polymer).

The hypoxia-sensitive moiety can be any moiety that can undergo a reaction or other structural change in response to a decrease in oxygen (e.g., in a solvent or physiological environment in contact with the amphiphilic polymeric material). For example, the hypoxia-sensitive group can undergo a reduction reaction or reactions in response to a decrease in oxygen. The reduction reaction or reactions can be catalyzed by an enzyme. In some embodiments, the decrease in oxygen can be the result of the localized depletion of oxygen caused by the activity of a glucose oxidizing agent oxidizing glucose in contact with the amphiphilic polymeric material. Thus, in some embodiments, the hypoxia is a side effect of an increase in glucose concentration near the amphiphilic polymeric material.

Representative hydrophobic hypoxia-sensitive moieties include nitro-substituted aryl groups. In some embodiments, the hypoxia-sensitive moiety is a nitroimidazole (e.g., a 2-nitroimidazole). The nitroimidazole can comprise one or more aryl group substituents (e.g., alkyl, halo, etc.) substituted on carbon and/or nitrogen atoms of the imidazole ring, i.e., in addition to the nitro group substituted on the imidazole ring. In some embodiments, the hypoxia-sensitive moiety can include more than one nitro group.

In some embodiments, a hydrophobic group or groups are covalently bound to the polymer. For example, a hydrophobic group can be based on a precursor molecule that includes an amino group that forms an amide linkage with a carboxylic acid group present on a hydrophilic polymer. In some embodiments, the amphiphilic polymeric material comprises poly(ethylene glycol) (PEG) and polyserine modified with 2-nitroimidazole via a thioether moiety.

Any suitable glucose oxidizing agent can be used. In some embodiments, the glucose oxidizing agent is an enzyme, such as glucose oxidase (GOx) (EC1.1.3.4), which oxidizes glucose to produce hydrogen peroxide and D-glucono-δ-actone, the cyclic form of gluconic acid.

In some embodiments, the insulin or bioactive derivative thereof can be human insulin, recombinant human insulin, insulin from a non-human animal source (e.g. bovine, porcine) or any other insulin, including insulin derivatives. In some embodiments, the insulin is of the same species as the intended recipient, i.e., human insulin for treatment of humans. The insulin or bioactive derivative thereof can include mixtures of different insulins and/or derivatives. The insulin or bioactive derivative thereof can include fast-acting insulins, rapid-acting insulin analogs, intermediate-acting insulins, and/or long-acting insulins. In some embodiments, the insulin or bioactive derivative thereof is a fast-acting or rapid-acting insulin.

Fast-acting insulins start to work within one to 20 minutes, peaking about one hour later and lasting from three to five hours. Fast-acting insulin takes about two hours to fully absorb into the systemic circulation. Fast-acting insulins include regular recombinant human insulin (such as HUMULIN™ marketed by Lilly, and NOVOLIN™, marketed by NovoNordisk). Bovine and porcine insulins, which differ in several amino acids to human insulin, but are bioactive in humans, are also fast acting insulins.

Rapid-acting insulins include insulins that have been modified or have altered locations of amino acids in order to enhance their rate of absorption. There are three types of rapid-acting commercial insulin analogs available: lispro insulin (Lysine-Proline insulin, sold by Eli Lilly as HUMALOG™), glulisine insulin (sold by Sanofi-Aventis as APIDRA™) and aspart insulin (sold by Novo Nordisk as NOVOLOG™).

Intermediate-acting insulin has a longer lifespan than short-acting insulin, but it is slower to start working and takes longer to reach its maximum strength. Intermediate-acting insulin usually starts working within 2-4 hours after injection, peaks somewhere between 4-14 hours and remains effective up to 24 hours. Types of intermediate-acting insulin include NPH (Neutral Protamine Hagedorn) and LENTE™ insulin. NPH insulin contains protamine which slows down the speed of absorption so that the insulin takes longer to reach the bloodstream but has a longer peak and lifespan.

Long-acting insulins include Eli Lilly's Humulin™ U (Ultralente™ human insulin (recombinant DNA origin) extended zinc suspension); and insulin glargine (LANTUS™ Aventis). Insulin glargine is a recombinant human insulin analog that can have up to 24 hour duration. It differs from human insulin by having a glycine instead of asparagine at position 21 and two arginines added to the carboxy-terminus of the beta-chain. LANTUS™ consists of insulin glargine dissolved in a clear aqueous fluid (100 IU, 3.6378 mg insulin glargine, 30 micrograms zinc, 2.7 mg m-cresol, 20 mg glycerol 85%, and water to 1 ml).

In some embodiments, the amphiphilic polymeric material forms a nanoparticle that contains the insulin or bioactive derivative thereof and the glucose oxidizing agent enclosed or entrapped within the interior of the nanoparticle (e.g., in pores or other interior spaces within the nanoparticle) or otherwise non-covalently associated with the polymeric material. In some embodiments, reduction of the hypoxia-sensitive moiety and/or oxidation of the hydrogen peroxide-sensitive moiety can disrupt the nanoparticle structure, allowing the insulin or a bioactive derivative thereof to be dispersed from the nanoparticle (e.g., by diffusion). In some embodiments, the amphiphilic polymeric material forms a vesicle (also referred to as a "polymersome") comprising a layer or layers (e.g., a bilayer) of polymer encapsulating the insulin or bioactive derivative thereof and the glucose oxidizing agent in an aqueous core. Reduction of the hypoxia-sensitive moiety (e.g., in response to hypoxia resulting from an increase in activity of the glucose oxidizing agent due to an increase in glucose) and/or oxidation of the hydrogen peroxide-sensitive moiety due to an increase in $H_2O_2$ can lead to disassembly of the vesicle and release of the insulin or derivative thereof.

In some embodiments, the nanoparticles and/or vesicles have an average diameter of between about 50 to about 500 nm. In some embodiments, the average diameter is between about 50 and about 250 nm. In some embodiments, the average diameter is between about 80 and about 160 nm (e.g., about 80, 85, 90, 95, 100, 105, 110, 115, 120, 125, 130, 135, 140, 145, 150, 155, or 160 nm). In some embodiments, the nanoparticles and/or vesicles have an average diameter (e.g., as measured via dynamic light scattering) of about 94 nm. In some embodiments, the nanoparticles and/or vesicles can be mono-disperse or nearly mono-disperse (e.g., wherein at least about 80% of the distribution lies within 15%, 10% or 5% of the median particle size).

In some embodiments, the compositions of the presently disclosed subject matter, e.g., the nanoparticles and/or vesicles, can be used to prepare microneedle arrays for the delivery of insulin or a bioactive derivative thereof. In some embodiments, the presently disclosed subject matter provides a microneedle array comprising a plurality of microneedles comprising vesicles, wherein the vesicles comprise an amphiphilic polymeric material comprises a polymer conjugated to a hydrogen peroxide-sensitive hydrophobic group and a hypoxia-sensitive hydrophobic group, wherein said hydrogen peroxide-sensitive group comprises a hydrogen peroxide-sensitive moiety that can be oxidized in the presence of a hydrogen peroxide to form a hydrophilic moiety and said hypoxia-sensitive hydrophobic group comprises a hypoxia-sensitive moiety that can be reduced in the presence of a hypoxic environment to form a hydrophilic moiety, and further wherein (i) an insulin or a bioactive derivative thereof and (ii) a glucose oxidizing agent are contained within said vesicle. In some embodiments, the microneedle array can comprise a plurality of microneedles wherein each of said plurality of microneedles has a length of between about 20 and about 1000 microns (e.g., about 20, 50, 100, 150, 200, 250, 300, 350, 400, 450, 500, 550, 600, 650, 700, 750, 800, 850, 900, 950, or about 1000 microns). In some embodiments, each of the plurality of microneedles has a length of between about 500 microns and about 700 microns. In some embodiments, each microneedle can have an approximately conical or pyramidal shape. In some embodiments, the tip of the microneedles can be less than about 100 microns, less than about 75 microns, less than about 50 microns, less than about 40 microns, less than about 30 microns, or less than about 20 microns. In some embodiments, the tip of each of the microneedles can be about 10 microns.

The microneedle array can comprise a plurality of microneedles, wherein the bases of microneedles are arranged in any suitable two-dimensional pattern. The microneedles can be arranged in a regular array (e.g., a square, rectangular, circular, oval or other shaped pattern) wherein the distance between individual microneedles remains the same or varies in a repeating fashion, or in an irregular array (e.g., wherein the distance between individual microneedles varies in no recognizable repeating fashion).

In some embodiments, the microneedle array can be provided as part of a skin patch. In some embodiments, the microneedle array can comprise one or more backing layers (e.g., to protect the microneedle array from moisture or physical insult (e.g., scratches). In some embodiments, the microneedle array can comprise a layer that extends outward from the array (e.g., coplanar to the base of the array) that comprises a skin-compatible adhesive for aiding in the attachment of the array to the skin.

The presently disclosed microneedle arrays can release insulin or a bioactive derivative thereof in a glucose-responsive or dependent manner. In some embodiments, the release rate of the insulin or bioactive derivative is dependent upon the concentration of glucose coming into contact with the array (e.g., the release rate is faster when the array in contact with higher concentrations of glucose). Thus, in some embodiments, the microneedle array is a closed-loop insulin delivery system.

In some embodiments, the presently disclosed subject matter provides a method of delivering an insulin or a bioactive insulin derivative to a subject in need thereof, the method comprising administering a composition (e.g., a nanoparticle and/or vesicle) of the presently disclosed subject matter to the subject. The administration can by any suitable route (e.g., oral, i.v., i.p., sub-cutaneous, transdermal, or via inhalation). In some embodiments, the method comprises providing a microneedle array of the presently disclosed subject matter, and applying said array to a skin surface of the subject. When glucose comes into contact with the microneedle array, it is oxidized, thereby (1) creating a hypoxic environment that results in the reduction of the hypoxia-sensitive moiety to form a hydrophilic moiety and (2) producing hydrogen peroxide that results in the oxidation of the hydrogen peroxide-sensitive moiety to form a hydrophilic moiety, leading to disruption of vesicles and release of an insulin or a bioactive insulin derivative contained in the vesicles. In some embodiments, the delivery of the insulin or bioactive insulin derivative is at a rate corresponding to the glucose concentration coming into contact with the microneedle array.

In some embodiments, one or more additional therapeutic agent is contained within the vesicles and/or microneedles and can be released along with the insulin or bioactive derivative thereof. In some embodiments, the additional therapeutic agent is water-soluble. In some embodiments, the additional therapeutic agent is a protein or protein derivative. In some embodiments, the additional therapeutic agent is an agent for treating diabetes or a complication thereof.

In some embodiments, the subject treated according to the presently disclosed subject matter is a human subject, although it is to be understood that the methods described herein are effective with respect to all vertebrate species, which are intended to be included in the term "subject."

More particularly, provided herein is the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Thus, embodiments of the methods described herein include the treatment of livestock, including, but not limited to, domesticated swine (pigs and hogs), ruminants, horses, poultry, and the like.

In some embodiments, the subject is diabetic. The subject can have type 1 or type 2 diabetes. In some embodiments, the subject can have a glucose metabolism disorder.

In some embodiments, the presently disclosed subject matter provides a method of preparing a microneedle array for the glucose-sensitive delivery of insulin or a bioactive derivative thereof. In some embodiments, the method can comprise:

(a) preparing an aqueous solution of a vesicle and/or nanoparticle of the presently disclosed subject matter;

(b) dispersing said aqueous solution into a mold comprising a plurality of microneedle cavities, thereby providing a filled mold;

(c) drying the filled mold to remove water; and (d) removing the mold to provide a microneedle array.

In some embodiments, the method can further comprise cross-linking polymeric materials in the microneedle array. For example, in some embodiments, a chemical cross-linker (e.g., N,N-methylenebisacrylamide) and/or photoinitiator can be added to the mold prior to drying. In some embodiments, the cross-linking can be performed by exposure to UV irradiation after the mold is removed.

In some embodiments, an additional polymer can be added to the mold prior to drying. The additional polymer can be the same or different from the hydrophilic polymer of the amphiphilic polymeric material. In some embodiments, the additional polymer is a modified hyaluronic acid, such as an alkylene-modified and/or an acrylate-modified hyaluronic acid.

In some embodiments, the filling of the mold in step (b) can be performed under vacuum and/or can involve centrifuging the mold (e.g., to aid in efficient and/or increased packing of the vesicles in the microneedle cavities). In some embodiments, the mold can be dried in a vacuum desiccator.

In some embodiments, the mold can comprise a polymer, such as silicone (e.g., polydimethylsiloxane (PDMS)). The mold can comprise about 10, 50, 100, 250, 500, 1000 or more microcavities. The tip-to-tip spacing between tips of the microcavities can be between about 100 microns and about 1000 microns (e.g., about 100, 150, 200, 250, 300, 350, 400, 450, 500, 550, 600, 650, 700, 750, 800, 850, 900, 950, or about 1000 microns).

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

In general, in vitro and in vivo results presented are Mean±the standard error of the mean. Statistical analysis was performed using Student's t-test or ANOVA test. With a p value <0.05, the difference between experimental groups and control groups were considered statistically significant.

Example 1

Representative Synthesis of Hypoxia-Sensitive Block Copolymers and Dual Hydrogen Peroxide and Hypoxia-Sensitive Block Copolymers All chemicals were purchased from Sigma-Aldrich (St. Louis, Mo., United States of America) unless otherwise specified and were used as received. Bromochloromethane was purchased from SynQuest Laboratories, Inc. (Alachua, Fla., United States of America). Poly-(ethylene glycol) amine (PEG2000-$NH_2$) was ordered from Laysan Bio, Inc. (Arab, Ala., United States of America). The deionized water was prepared by a Millipore NanoPure purification system (resistivity higher than 18.2 MΩ $cm^{-1}$) (Merck Millipore, Billerica, Mass., United States of America).

Figure 2A:
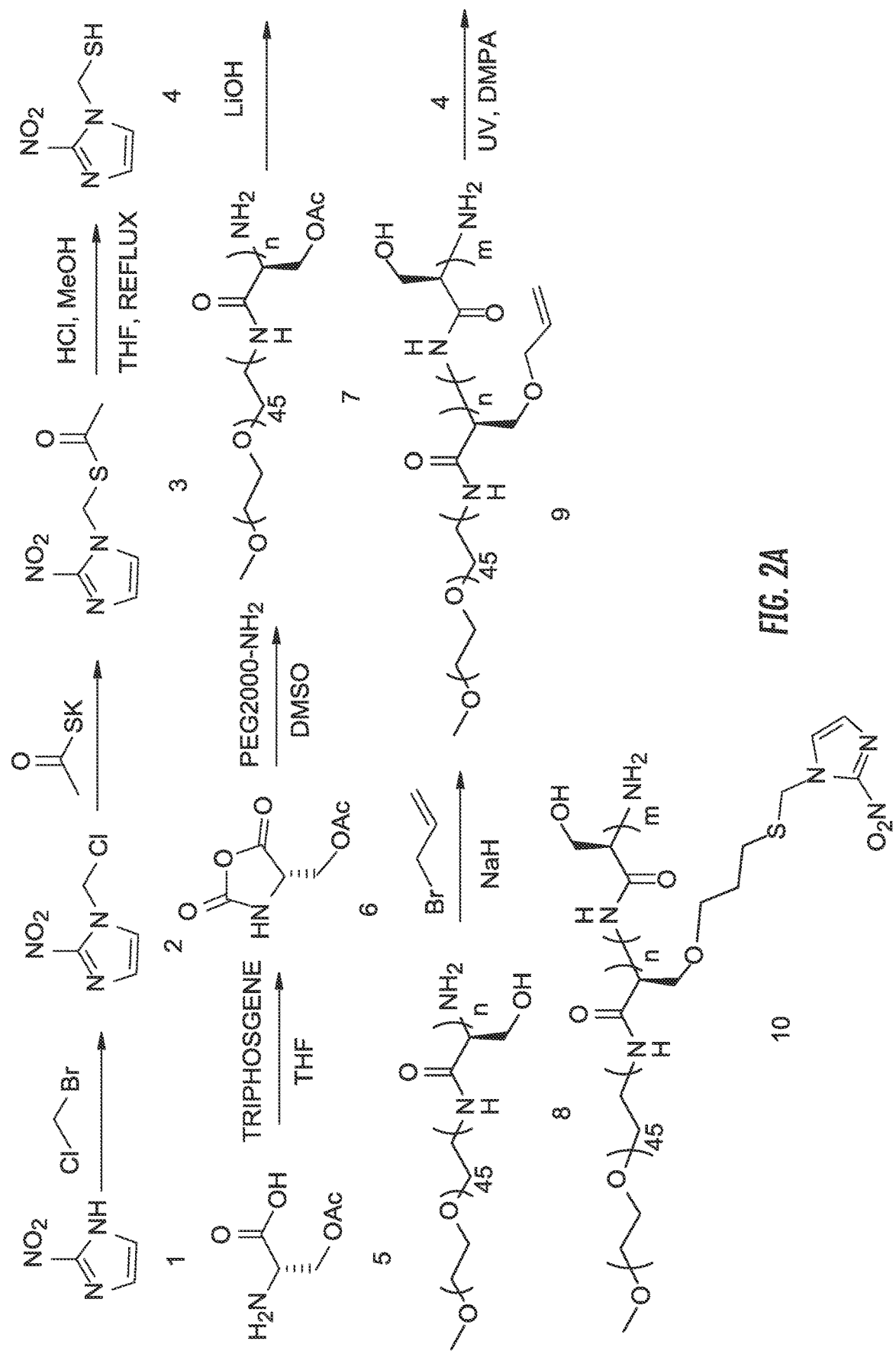
FIG. 2A is a schematic diagram showing the chemical synthesis of an amphiphilic block copolymer (10, i.e., "PEG-Poly(Ser-S-NI)") comprising poly(ethylene glycol) (PEG) and polyserine wherein the polyserine is modified to comprise thioether and nitroimidazole groups.
Figure 2B:
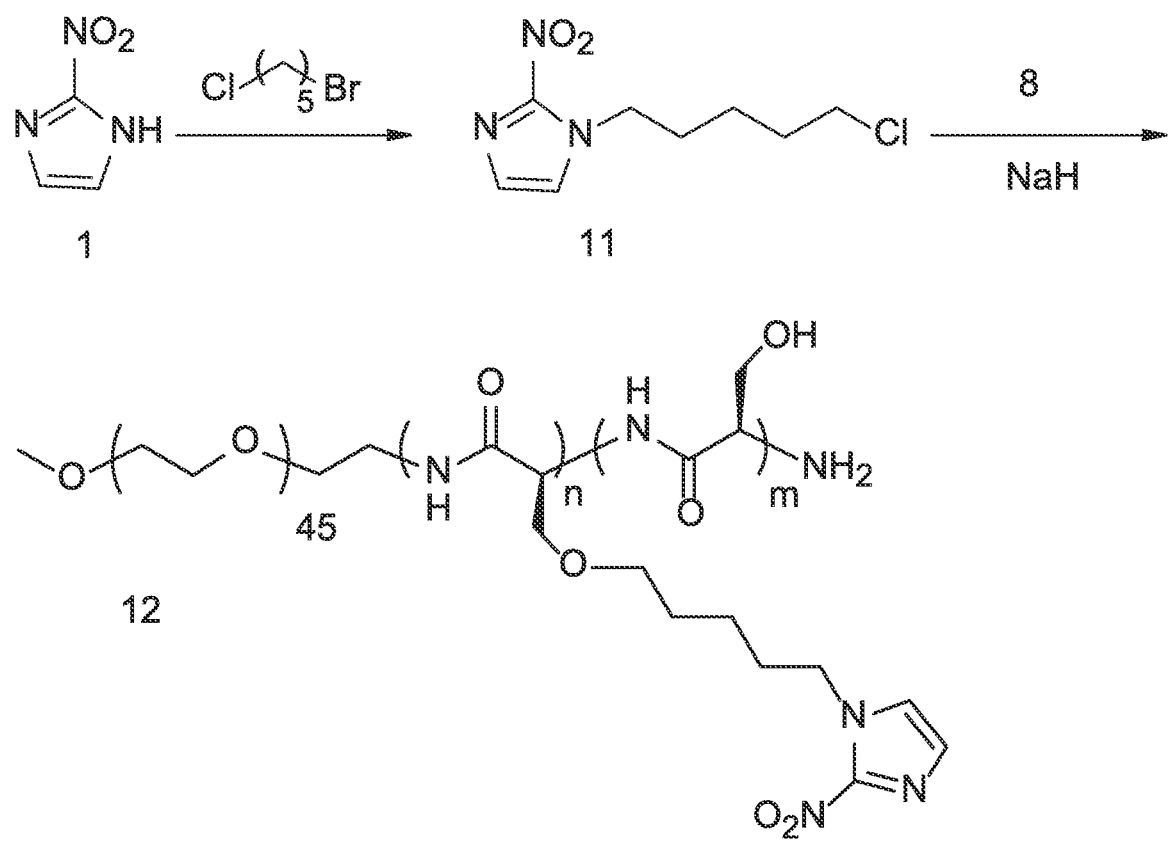
FIG. 2B is a schematic diagram showing the chemical synthesis of a amphiphilic block copolymer (12, i.e., "PEG-Poly(Ser-NI)"), similar to that shown in FIG. 2A, comprising PEG and polyserine, but where the polyserine is modified with only a nitroimidazole group.

The syntheses of dual-sensitive PEG-Poly(Ser-S-NI) and hypoxia sensitive PEG-Poly(Ser-NI) were performed as shown in FIGS. 2A and 2B. For the synthesis of PEG-Poly(Ser-S-NI) (10 of FIG. 2A), first, 1-(chloromethyl)-2-nitro-1H-imidazole (2 of FIG. 2A) was prepared based on a procedure as described in Bonnet et al., (Biorg, Med. Chem., 2014, 22, 2123-2132). Briefly, bromochloromethane (5.7 mL, 88 mmol) was added to a stirred solution of 2-nitroimidazole (1) (500 mg, 4.4 mmol) in anhydrous dimethylformamide (DMF) (30 mL), and then $Cs_2CO_3$ (2.87 g, 8.8 mmol) was added. The reaction was stirred at 18° C. for 16 h. The reaction mixture was partitioned between ethyl acetate (200 mL) and $H_2O$ (50 mL) three times. The organic phase was washed with water and brine three times and then was dried by solvent evaporation. The crude product was suspended in ethyl acetate (3 ml), and the white solid was filtered off. The filtrate was concentrated and dried to give 1-(chloromethyl)-2-nitro-1H-imidazole (2) (310 mg, 43.5%) as an oil, which was used without further purification. $^1$H NMR (300 MHz, DMSO-$d_6$, δ): 7.88 (d, 1H, H-5), 7.27 (d, 1H, H-4), 6.27 (s, 2H, $CH_2$).

Then, potassium thioacetate (390 mg, 3.4 mmol) was added to a stirred solution of 1-(chloromethyl)-2-nitro-1H-imidazole (2) (550 mg, 3.4 mmol) in anhydrous DMF (15 mL), and the mixture was stirred at 18° C. for 16 h. The reaction mixture was partitioned between ethyl acetate (200 mL) and $H_2O$ (50 mL). The organic phase was washed with $H_2O$ and brine for 3 times, then was dried and the solvent was evaporated. The residue was purified by column chromatography, eluting with 30% ethyl acetate/petroleum ether, to give S-[(2-nitro-1H-imidazol-1-yl)methyl] ethanethioate (3) (450 mg, 66.2%) as a white solid. $^1$H NMR (300 MHz, DMSO-$d_6$, δ): 7.67 (d, 1H, H-5), 7.18 (d, 1H, H-4), 5.79 (s, 2H, $CH_2$), 2.41 (s, 3H, $CH_3$).

Further to procedures described in Bonnet et al., (Biorg, Med. Chem., 2014, 22, 2123-2132) and Matsumoto et al., (Macromolecules, 2008, 41, 5674-5680), S-[(2-nitro-1H-imidazol-1-yl)methyl] ethanethioate (3) (5 g, 25 mmol) was placed in a flask and dissolved in tetrahydrofuran (THF) (30 mL). Hydrogen chloride in methanol (60 mL, 1.25 M) was added to the mixture. After stirring for 6 h at 50° C., the reaction was quenched by the addition of water. The aqueous layer was extracted with dichloromethane, and the combined organic layer was washed with $NaHCO_3$ solution, dried over $Na_2SO_4$, and concentrated in vacuo to yield (2-nitro-1H-imidazol-1-yl)methanethiol (4) (2 g, 40%), which was used without further purification. $^1$H NMR (300 MHz, DMSO-$d_6$, δ): 7.39 (d, 1H, H-5), 6.93 (d, 1H, H-4), 5.30 (s, 2H, $CH_2$).

As further shown in FIG. 2A, PEG-Polyserine (8) was prepared based on a previously published method. See Tai et al., Biomacromolecules, 2014, 15, 3495-3502. Briefly, triphosgene (3.92 g, 17 mmol) was added to a stirred suspension of O-acetyl-L-serine (5) (5 g, 34 mmol) in 200 mL of anhydrous THF. The reaction mixture was stirred at 48° C. for 2-3 h, and the suspension gradually turned clear, which indicated that O-acetyl-L-serine was consumed and the reaction completed. After cooling to room temperature, the reaction mixture was concentrated under vacuum to give crude O-acetyl-L-serine N-carboxyanhydride (6). The crude product was purified by silica gel chromatography (the silica gel was dried at 140° C. under vacuum for 8 h before use) using petroleum ether/ethyl acetate (v/v, 2/1 then 1/1) as eluent. Light yellow oil was obtained with yield of 83%. $^1$H NMR (300 MHz, $CDCl_3$, δ): 7.14 (s, 1H), 4.67 (s, 1H), 4.60 (d, 1H), 4.32 (d, 1H), 2.11 (s, 3H).

The O-acetyl-L-serine N-carboxyanhydride (6) solution (4.8 g in 10 mL of dry DMSO) was then quickly added into a stirred solution of $PEG_{2000}$-$NH_2$ (0.925 g, 0.46 mmol) in 80 mL of anhydrous dimethyl sulfoxide (DMSO). The polymerization reaction was carried out under vacuum at room temperature for 48 h (vacuum can remove byproduct $CO_2$ from viscous reaction mixture and facilitate polymerization). The product PEG-Poly(AcO-Ser) (7) was precipitated from the reaction by 400 mL of diethyl ether.

PEG-Poly(AcO-Ser) (7) (crude product from last step) was further suspended in 100 mL of distilled water. The viscous suspension was stirred at room temperature under a stream of nitrogen gas for 30 min to remove the trace diethyl ether. Lithium hydroxide (1.3 g, 31 mmol) was added into the reaction and the reaction was stirred at room temperature for 1.5 h. When the reaction mixture completely turned clear, 2 N HCl solution was added to neutralize the reaction solution. The reaction mixture was then transferred to a dialysis tubing (MWCO: 1000 Da; Spectra Lab, Rockleigh, N.J., United States of America) and dialyzed against water for 40 h. The resulting solution was lyophilized to give PEG-Polyserine (8): 1.74 g, two step yield=36%; Mw, 34232 g/mol; Mn, 29313 g/mol; Mw/Mn, 1.17. $^1$H NMR (300 MHz, $D_2O$, δ): 4.50 (br s, 7H), 3.88 (br s, 27H), 3.67 (s, $CH_3$—O—$CH_2$—$CH_2$—O—, 180H).

PEG-Poly(Ser-allyl ether) (9) was prepared based on procedures as previously described. See Napsoli et al., Macromolecules, 2001, 34, 8913-8917. In an ice-water bath, PEG-Polyserine (8) (1 g) was dissolved in anhydrous DMF (40 mL) followed by the slow addition 0.5 equiv of sodium hydride (0.2 g, 60%, 5 mmol). Thirty minutes later, 0.5 equiv of allyl bromide (0.36 mL, 4 mmol) was added dropwise. After stirring at room temperature for another 16 h, the reaction was stopped by adding 20 ml of water. The reaction mixture was then transferred to dialysis tubing (MWCO: 1000 Da; Spectra Lab, Rockleigh, N.J., United States of America) and dialyzed against water for 24 h. The resulting solution was lyophilized and dried to give crude product PEG-Poly(Ser-Allyl Ether) (9). The crude product 9 was collected by centrifugation and washed with diethyl ether and hexane, respectively. The obtained solid was dissolved in dichloromethane, and after filtration and evaporation of the solvent, a white solid polymer PEG-Poly(Ser-allyl ether) (9) (0.8 g, yield 80%) was finally collected. $^1$H NMR (300 MHz, $CDCl_3$, δ): 5.85 (br s, —$OCH_2$CH═$CH_2$), 5.19 (br s, —$OCH_2$CH═$CH_2$), 4.67 and 3.98 (br s, —NHCO—CHCH$_2$—), 3.66 (br s, $CH_3$—O—$CH_2$—$CH_2$—O— of PEG, —$OCH_2$CH═$CH_2$).

In a quartz flask, (2-nitro-1H-imidazol-1-yl)methanethiol (4) (385 mg, 2.4 mmol, 2 equiv. of the allyl groups) and photoinitiator (2,2-dimethoxy-2-phenyl acetophenone, DMPA, 15 mg) were added to the PEG-Poly(Ser-allyl ether) (9) solution (211.5 mg, in 20 mL THF), followed by purging with nitrogen for 10 min. The quartz flask was sealed and irradiated by UV (365 nm, 16 mW) for 30 min. The reaction mixture was then stirred at room temperature overnight. After evaporation of the solvent and washing with ethyl ether, PEG-Poly(Ser-S-NI) (10) in a yellow solid form was obtained (300 mg, 85%). $^1$H NMR (300 MHz, CDCl$_3$, δ): 7.33 (d, NI-H-5), 6.87 (d, NI-HA), 5.74 (br s, —OCH$_2$CH=CH$_2$), 5.24-5.05 (br m, —OCH$_2$CH=CH$_2$, NI-CH$_2$—), 4.5 and 3.85 (br s, —NHCO—CHCH$_2$—), 3.50 (br s, CH$_3$—O—CH$_2$—CH$_2$—O— of PEG, —OCH$_2$CH=CH$_2$). Based on the UV-vis spectrum of the obtained PEG-Poly(Ser-S-NI) polymer, approximately 32% of the (2-nitro-1H-imidazol-1-yl)methanethiol were conjugated to PEG-Poly(Ser-S-NI).

As shown in FIG. 2, 1-Bromo-5-chloropentane (25 mL, 35 mmol) was added to a stirred solution of 2-nitroimidazole (1) (200 mg, 1.75 mmol) in anhydrous DMF (30 mL), and then caesium carbonate (1.14 g, 3.5 mmol) was added. The reaction was stirred at 18° C. for 16 h. The reaction mixture was partitioned between ethyl acetate (200 mL) and H$_2$O (50 mL) three times. The organic phase was washed with H$_2$O and brine three times, followed by solvent evaporation. The crude product was purified by column chromatography, eluting with petroleum ether first, to extract the 1-bromo-5-chloropentane, and then eluting with ethyl acetate, to give 1-(5-chloropentyl)-2-nitro-1H-imidazole (11) (75%) as an oil. $^1$H NMR (300 MHz, DMSO-d$_6$, δ): 7.70 (d, 1H, H-5), 7.19 (d, 1H, H-4), 4.39 (m, 2H, CH$_2$), 3.64 (m, 2H, CH$_2$), 1.78 (m, 4H, CH$_2$), 1.40 (m, 2H, CH$_3$).

In an ice-water bath, PEG-Polyserine (8) (0.5 g) was dissolved in anhydrous DMF (20 mL) followed by the slow addition 0.5 equiv of sodium hydride (0.1 g, 60%, 2.5 mmol). Thirty minutes later, 0.5 equiv of 1-(5-chloropentyl)-2-nitro-1H-imidazole (11) was added dropwise. After stirring at room temperature for another 16 h, the reaction was stopped by adding 20 ml of water. The reaction mixture was then transferred to a dialysis tubing (MWCO: 1000 Da; Spectra Lab, Rockleigh, N.J., United States of America) and dialyzed against water for 24 h. The resulting solution was lyophilized to give crude product PEG-Poly(Ser-NI) (12). The crude product 12 was collected by centrifugation and washed with diethyl ether and hexane, respectively. The obtained solid was dissolved in dichloromethane, and after filtration and evaporation of the solvent, a white solid polymer PEG-Poly(Ser-NI) (12) (yield 67%) was finally collected. $^1$H NMR (300 MHz, CD$_2$Cl$_2$, δ): 7.12 (d, NI-H-5), 6.15 (d, NI-H-4), 4.37 and 3.83 (br s, —NHCO—CHCH$_2$—), 3.60 (br s, CH$_3$—O—CH$_2$—CH$_2$—O— of PEG, —O—CH$_2$), 1.62 (bs, —CH$_2$CHr-).

Example 2

Figure 3H:
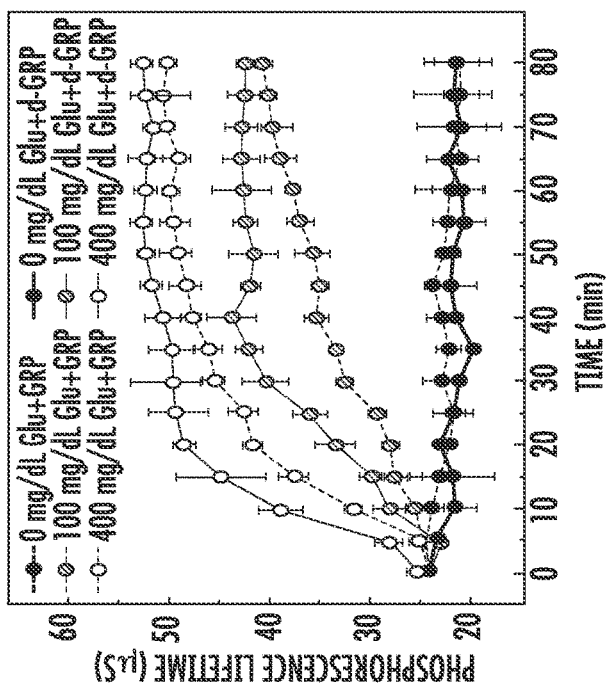
FIG. 3H is a graph showing the phosphorescence lifetime profile for glucose oxidase (GOx)-loaded dual-sensitive glucose-responsive polymersomes (d-GRPs, circles linked by solid lines) or GOx-loaded non-hydrogen peroxide sensitive glucose-responsive polymersomes (GRPs, circles linked by dotted lines) incubated with different glucose (Glu) concentration solutions (i.e., 0 (filled circles), 100 (striped circles), or 400 (open circles) milligrams per deciliter (mg/dL)) containing an oxygen concentration molecule probe.

Synthesis and Characterization of Dual-Sensitive Glucose-Responsive Polymersomes The d-GRPs were prepared through the solvent evaporation method. Briefly, 40 mg of PEG-poly(Ser-S-NI) was dissolved in 1.5 mL of THF. A total of 3 mL of aqueous insulin solution containing insulin (40 mg) and GOx (4 mg) was slowly dropped into the polymer solution while stirring. Then, the nitrogen gas slowly flowed through the mixture to accelerate THF evaporation in a chemical fume hood. After the removal of THF, the d-GRP suspension was collected by centrifugation at 14,000 rpm and washed with PBS buffer for several times. The final d-GRP suspension was stored at 4° C. for later study. The insulin loading capacity (LC) of d-GRPs was determined as 3.2% by measuring the loaded insulin content using a Coomassie Plus protein assay (Thermo Fisher Scientific Inc., Waltham, Mass., United States of America). The zeta potential and size distribution were measured on the Zetasizer (Nano ZS, Malvern Instruments Ltd., Malvern, United Kingdom). The transmission electron microscopy (TEM) images of d-GRPs were obtained on a JEOL 2000FX TEM instrument (JEOL USA, Inc., Peabody, Mass., United States of America). See FIG. 3A. Non-hydrogen peroxide-sensitive GRPs were prepared via an analogous method using PEG-Poly(Ser-NI). See FIG. 4.

The sensitivity of d-GRPs and GRPs to H$_2$O$_2$ was assessed using a fluorimetric hydrogen peroxide assay kit (Sigma-Aldrich, St. Louis, Mo., United States of America) according to the manufacturer's protocol. d-GRPs or GRPs were added at different concentrations to the H$_2$O$_2$ solution (5 μM). After 10 min reaction with H$_2$O$_2$, the solution of red peroxidase substrate and peroxidase was added, and incubated at room temperature for 20 min. The fluorescence intensity was measured on a microplate reader with excitation and emission wavelengths of 540 and 590 nm.

Oxygen consumption rate (OCR) was determined by using MitoXpress (Cayman Chemical, Ann Arbor, Mich., United States of America) according to the manufacturer's protocol. Briefly, 200 μL GOx-loaded d-GRPs or GRPs solution suspended in PBS buffer with 0, 100 or 400 mg/dL glucose containing 10 μL MitoXpress probe was placed in a 96-well plate, and the plate was measured on a microplate reader at the excitation/emission wavelength of 380/650 nm at 37° C. Each sample well was measured repeatedly every 5 min, by taking two intensity readings at delay times of 30 and 70 μs and gate time of 30 μs. Obtained TR-F intensity signals for each sample well were converted into phosphorescence lifetime (μs) [T] values as follows: T=(70−30)/In (F1/F2), where F1 and F2 are the TR-F intensity signals at delay times 70 μs and 30 μs. The resulting increasing lifetime [T] reflects the sample's oxygen concentration.

Example 3

In Vitro Glucose-Responsive Insulin Release of GRPs and D-GRPs

To evaluate the glucose-responsive characteristics of d-GRPs, d-GRPs were mixed with 1.5 mL PBS solution (NaCl, 137 mM; KCl, 2.7 mM; Na$_2$HPO$_4$, 10 mM; KH$_2$PO$_4$, 2 mM; pH 7.4), to which 100 μM NADPH and 5 μg/mL cytochrome c reductase were added. Various amounts of glucose were added to each suspension to reach final glucose concentration of 0 mg/dL, 100 mg/dL and 400 mg/dL. The suspensions were incubated at 37° C. in a container with an oxygen concentration of 21% as regulated with a mass-flow meter. At indicated time points, 100 μL of the d-GRPs mixture was taken out and the released insulin was separated by a centrifugal filter (100,000 Da molecular mass cutoff, Merck Millipore, Billerica, Mass., United States of America). The insulin concentration was examined using a Coomassie Plus protein assay. The absorbance was detected at 595 nm on the INFINITE® 200 PRO multimode plate reader (Tecan Group Ltd., Zurich, Switzerland), and the insulin content was calibrated with an insulin standard curve. For plotting the UV-Vis absorption of d-GRPs solution, the absorbance intensity was measured at 330 nm at the set time. To access the d-GRPs' ability to adapt to cyclical changes in glucose levels, d-GRPs were first incubated in PBS buffer with 100 mg/dL glucose, 100 μM NADPH and 5 μg/mL cytochrome c reductase for 15 min. At that point, the d-GRP samples were separated using a centrifugal filter (100,000 Da molecular mass cutoff, Merck Millipore, Billerica, Mass., United States of America), and then incubated in 400 mg/dL glucose for another 15 min. This cycle was repeated numerous times. The released insulin was measured using the same method mentioned above. The far-UV circular dichroism (CD) spectra of the native and released insulin from d-GRPs (0.1 mg/mL) were analyzed using an Aviv CD spectrometer (Aviv Biomedical Inc., Lakewood, N.J., United States of America).

Example 4

Fabrication and Characterization of GRPs-Loaded Microneedle (Mn)-Array Patch

Acrylate-modified hyaluoric acid (m-HA) was synthesized as previously described. See Yu et al., Proc. Natl. Acad. Sci. USA, 2015, 112, 8260-8265. Briefly, 1.0 g of hyaluronic acid was dissolved in 50 mL of DI water at 4° C., to which 0.8 mL of methacrylic anhydride was added dropwise. The reaction solution was adjusted to pH 8-9 by the addition of 5N NaOH and stirred at 4° C. for 24 h. The resulting polymer was precipitated in acetone, followed by washing with ethanol for 3 times. The product re-dissolved in DI water and the solution was dialyzed against DI water for 2 days. The lyophilized m-HA was produced with a yield of 87.5%. The degree of modification was calculated to be 15% by comparing the ratio of the areas under the proton peaks at 5.74 and 6.17 ppm (methacrylate protons) to the peak at 1.99 ppm (N-acetyl glucosamine of hyaluronic acid) after performing a standard deconvolution algorithm to separate closely spaced peaks. $^1$H NMR (300 MHz, D$_2$O, δ): 1.85-1.96 (m, 3H, CH2=C(CH$_3$)CO), 1.99 (s, 3H, NHCOCH$_3$), 5.74 (s, 1H, CH$^1$H$^2$=C(CH$_3$)CO), 6.17 (s, 1H, CH$^1$H$^2$=C(CH$_3$)CO).

Microneedles (MNs) were fabricated using uniform silicone molds from Blueacre Technology Ltd. (Dundalk, Ireland). Each needle had a 300 μm diameter base tapering to a height of 600 μm with a tip diameter of around 10 μm. The needles were arranged in a 20×20 array with 600 μm tip-to-tip spacing. To fabricate d-GRP-loaded MNs, the d-GRPs suspension was first deposited by pipet onto the MN mold (100 μL/array). See FIG. 8. Afterwards, molds were placed under vacuum (600 mmHg) for 5 min to remove bubbles and increase viscosity. Then, the covered molds were centrifuged using a Hettich Universal 32R centrifuge (Hettich GmbH & Co. KG, Tuttlingen, Germany) for 20 min at 2000 rpm. The process was repeated for three times until the d-GRP layer was dried under vacuum. Afterwards, a piece of 4 cm×9 cm silver adhesive tape was applied around the 2 cm×2 cm micromold baseplate to keep the morphology of MNs. Finally, 3 mL m-HA solution containing N,N'-methylenebisacrylamide (MBA, w/v=2%) and photoinitiator (Irgacure 2959, w/v=0.5%) was added into the prepared micromold reservoir and dried at 25° C. in a vacuum dessicator overnight. After desiccation, the MN-arrays patch was carefully separated from the silicone mold and polymerized using a short UV irradiation (wavelength: 365 nm). The resulting MN-array patches were stored in a sealed six well container for later study. The morphology of the MNs was characterized on a FEI Verios 460 L field-emission scanning electron microscope (FESEM) (FEI, Hillsboro, Oreg., United States of America).

The mechanical strength of MNs with a stress-strain gauge was measured by pressing MNs against a stainless steel plate. The initial gauge was set as 2.00 mm between the MNs tips and the stainless steel plate, with 10.00 N as load cell capacity. The speed of the top stainless steel plate movement towards the MN-array patch was 0.1 mm/s. The failure force of MNs was recorded as the needle began to buckle.

Example 5

In Vivo Studies in Diabetic Mice

The in vivo efficacy of MN-array patches for diabetes treatment was evaluated on STZ-induced adult diabetic mice (male C57B6, Jackson Lab, U.S.A.). The animal study protocol was approved by the Institutional Animal Care and Use Committee at North Carolina State University and University of North Carolina at Chapel Hill. The plasma-equivalent glucose was measured from tail vein blood samples (~3 μL) of mice using the Clarity GL2Plus glucose meter (Clarity Diagnostics, Boca Raton, Fla., United States of America). Mouse glucose levels were monitored for two days before administration, and all mice were fasted overnight before administration. Five mice for each group were selected to be transcutaneously treated with blank MNs containing only m-HA, MNs loaded with human recombinant insulin, MNs loaded with d-GRPs containing insulin and enzyme (d-GRP(E+I)), or MNs loaded with d-GRPs containing insulin only (d-GRP(I)) on the dorsum with the insulin dose of 10 mg/kg for each mouse. The glucose levels of each mouse were monitored over time. In order to measure the plasma insulin concentration in vivo, 25 μL of blood sample was drawn from the tail vein of mice at indicated time points. The serum was isolated and stored at −20° C. until assay. The plasma insulin concentration was measured using a Human Insulin ELISA kit according to the manufacturer's protocol (Calbiotech, El Cajon, Calif., United States of America).

A glucose tolerance test was conducted to confirm the in vivo glucose responsiveness of MNs 1.5 hour post administration of d-GRP(E+I)-loaded MNs and insulin-loaded MNs. Briefly, mice were fasted overnight and administrated with d-GRP(E+I)-loaded MNs and insulin-loaded MNs with insulin dose of 10 mg/kg for each mouse, and then a glucose solution in PBS was intraperitoneally injected into all mice at a dose of 1.5 g/kg. The glucose levels were monitored over time after injection. The glucose tolerance test on healthy mice was used as control. Similarly, the healthy mice utilized to assess hypoglycemia were administered with insulin-loaded MNs or d-GRP(E+I)-loaded MNs, but were not subjected to a glucose challenge.

To assess the biocompatibility of the MN-array patch, pure HA MNs, d-GRP(E)-loaded MNs, and GRP(E)-loaded MNs were transcutaneously injected at different spots on the backs of the same animal (GOx dose: 3 mg/kg). After 24 h, the MNs were replaced with the same MNs at the same spot. Mice were euthanized by CO$_2$ asphyxiation 24 h following the second injection and the surrounding tissues were excised. The tissues were fixed in 10% formalin, then embedded in paraffin, cut into 5 μm sections, and stained using hematoxylin and eosin (H&E) and fluorescent TUNEL staining for histological analysis.

The in vitro cytotoxicity of bare d-GRPs was measured by 3-(4,5)-dimethylthiahiazo(-z-yl)-3,5-di-phenytetrazolium-romide (MTT) assay towards HeLa cells. Briefly, HeLa cells were seeded in 96-well plate at a density of 6000 cells per well. After 24 h incubation in 200 μL of Dulbecco's Modified Eagle Medium (DMEM) with 10% fetal bovine growth serum (FBS), serial dilutions of bare d-GRPs ranging from 0.1 to 1 mg/mL were added into wells. After 24 h incubation, thiazolyl blue solution (5 mg/mL) was added into wells and incubated with cells for another 4 h. After removing the culture media, the purple formazan crystal was dissolved in 150 μL of DMSO. The absorbance of the plates was read at 570 nm, which is directly proportional to the viable cell number, was measured on multimode plate reader.

Example 6

Discussion of Examples 1-5

The diblock copolymer (PEG-Polyserine) was first synthesized via amine-initiated ring-opening as previously reported. See Tai et al., Biomacromolecules, 2014, 15(10), 3495-3502. The (2-nitroimidazol-1-yl)methanethiol, which rendered the polymer sensitive to hypoxia and $H_2O_2$, was conjugated to the hydroxyl group of the serine residue through an allyl ether (PEG-Poly(Ser-S-NI)). See FIG. 2A. For comparison purposes, we also synthesized PEG-Poly (Ser-NI) without the sulfonate by incorporating the hydroxyl groups of PEG-Polyserine with 1-(5-chloropentyl)-2-nitro-imidazole (see FIG. 2B), which is only able to respond to hypoxia. PEG-Poly(Ser-NI) serves as a control to confirm the importance of the $H_2O_2$ elimination ability of PEG-Poly(Ser-S-NI).

Figure 4:
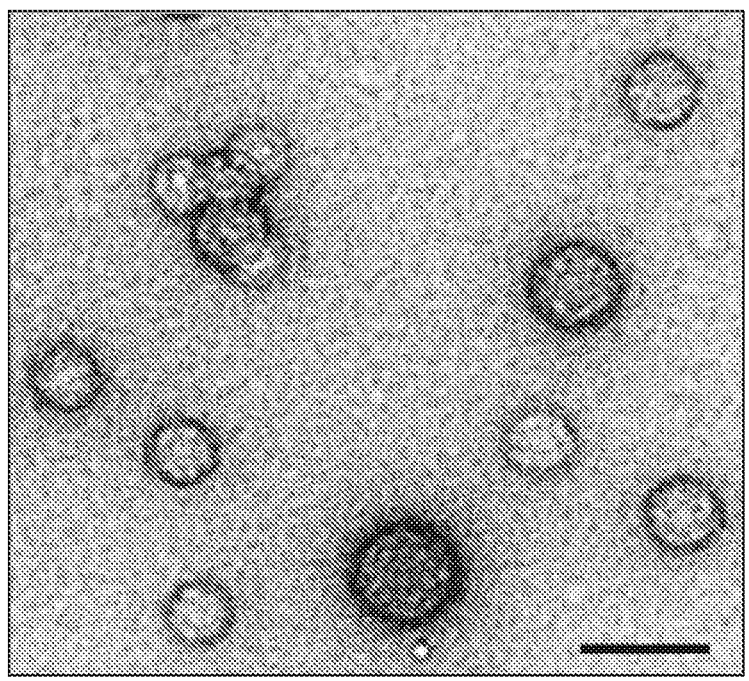
FIG. 4 is a transmission electron microscopy (TEM) micrograph image of non-hydrogen peroxide sensitive glucose-responsive polymersomes encapsulating insulin and glucose oxidase (GOx). The scale bar in the lower right represents 200 nanometers (nm).

The d-GRPs with encapsulated cargoes were formed by self-assembly of PEG-Poly(Ser-S-NI) through a solvent evaporation method. See Mo et al., Chem. Soc. Rev., 2014, 43(10), 3595-3629; and Tai et al., Biomacromolecules, 2014, 15(10), 3495-3502. As shown in FIG. 3A, the transmission electron microscopy (TEM) image showed that the d-GRPs had a spherical structure, and a bilayer membrane with a thickness of around 20 nm was clearly observed. The average diameter was measured as 94 nm by dynamic light scattering (DLS). See FIG. 3B. The successful encapsulation of insulin was further confirmed by fluorescence microscopy imaging of the d-GRPs with FITC-labeled insulin. See FIG. 3D. Meanwhile, non-$H_2O_2$ sensitive GRPs entrapping insulin and GOx were also prepared from PEG-Poly(Ser-NI) with the similar morphology and size as a control (FIG. 4).

Figure 3G:
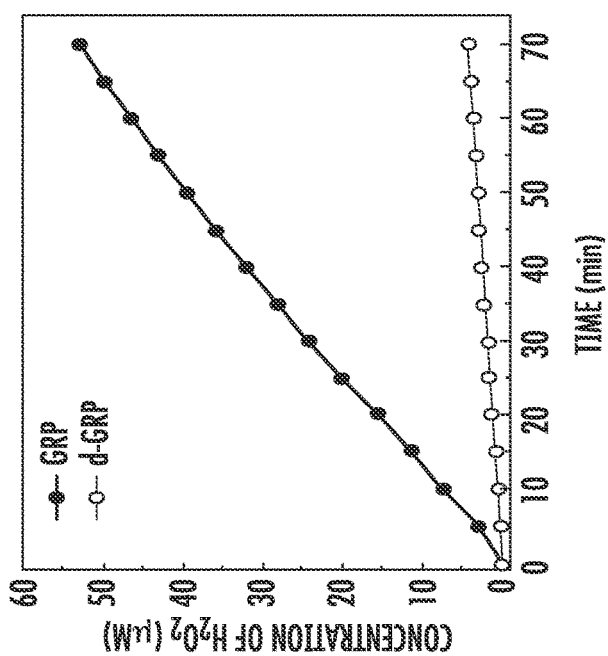
FIG. 3G is a graph showing the hydrogen peroxide generation rate of glucose oxidase (GOx)-loaded dual-sensitive glucose-responsive polymersomes (d-GRPs, open circles) or GOx-loaded non-hydrogen peroxide sensitive glucose-responsive polymersomes (GRPs, filled circles) incubated in a 400 milligram per deciliter (mg/dL) glucose solution.

The sensitivity of d-GRPs and GRPs to $H_2O_2$ was first assessed by measuring the concentration of $H_2O_2$ using a fluorimetric assay kit for hydrogen peroxide. The initial $H_2O_2$ solution (5 μM) showed high emission intensity after reaction with a peroxidase substrate. See FIG. 3F. However, addition of d-GRPs into the $H_2O_2$ solution produced a decline in fluorescence intensity. Furthermore, the reduction in intensity was dependent on the d-GRP concentration, while no significant change in the concentration of $H_2O_2$ occurred after incubation with GRP controls. Also, the $H_2O_2$ elimination capability was assessed through incubation of GOx-loaded vesicles with glucose. As shown in FIG. 3G, $H_2O_2$ generated rapidly due to the oxidation of glucose when incubating GRPs in PBS buffer [137 mM NaCl, 2.7 mM KCl, 10 mM $Na_2HPO_4$, 2 mM $KH_2PO_4$ (pH 7.4)] comprising 400 mg/dL glucose, while the produced $H_2O_2$ appeared to be almost eliminated by d-GRPs.

In order to evaluate the glucose-responsive capability of d-GRPs, vesicles were incubated with PBS buffer containing various concentrations of glucose, including a typical hyperglycemic level (400 mg/dL), a normoglycemia level (100 mg/dL), and a control level (0 mg/dL). In the presence of high glucose level, the dissolved oxygen was rapidly consumed due to the oxidation of glucose catalyzed by GOx. Using an oxygen-sensitive phosphorescent molecular probe (see Will et al., Nat. Protoc., 2006, 1(6), 2563-2572), a relatively lower oxygen level was generated in the d-GRPs under the hyperglycemia level compared to the other two control samples. See FIG. 3H. The oxygen concentration rapidly decreased within the vesicles and reached equilibrium within 20 min. Moreover, a slower oxygen consumption rate and higher oxygen level was observed when incubating GRPs with the same concentration in glucose solution. Without being bound to any one theory, it is believed that the lower oxygen level in the d-GRPs sample can be attributed to the $H_2O_2$ elimination ability of PEG-Poly(Ser-S-NI), which avoids the deactivation of GOx.

Figure 3I:
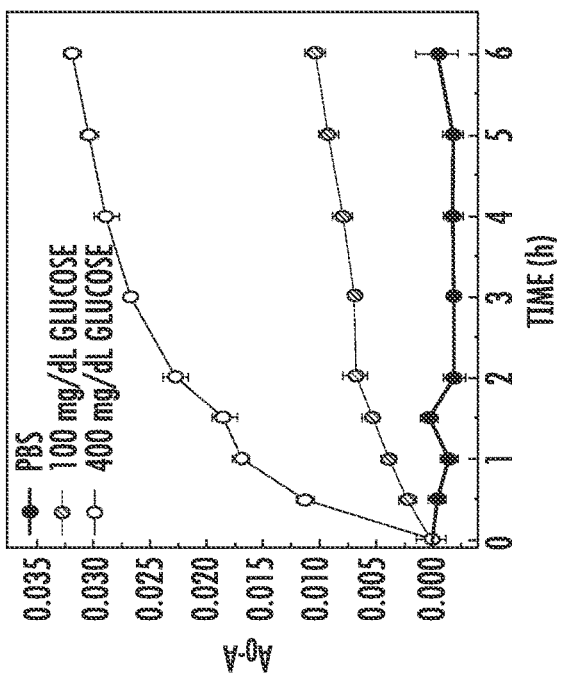
FIG. 3I is a graph showing the decrease in ultraviolet (UV) absorption at 330 nanometers (nm) of dual-sensitive glucose-responsive polymersomes (d-GRPs) in different glucose concentration solutions (0 (PBS, filed circles), 100 (striped circles), or 400 (open circles) milligrams per deciliter (mg/dL)) at 37 degrees Celsius. Error bars indicate s.d. (n=3).

Under such hypoxic condition, the NI groups were reduced by NADPH catalyzed by the reductase. See Yu et al., Proc. Natl. Acad. Sci. USA, 2015, 112(27), 8260-8265; Nunn et al., Eur. J. Nucl. Med., 1995, 22(3), 265-280; and Takawawa et al., Stroke, 2008, 39(5), 1629-1637. Correspondingly, the characteristic absorbance of NI at 330 nm gradually declined over time, confirming the conversion of hydrophobic NI groups to hydrophilic 2-aminoimidazoles groups. See FIG. 3I. Due to the generation of hydrophilic 2-aminoimidazoles and sulfone on PEG-Poly(Ser-S-NI), the d-GRPs began to dissociate and subsequently released the encapsulated cargoes. The corresponding change in morphology and size were clearly observed by transmission electron microscopy and dynamic light scattering. See FIGS. 3A and 3C. Furthermore, the release of FITC-labeled insulin was validated using fluorescence microscopy. As shown in the 2.5 D fluorescence images, the d-GRPs contain less insulin and a present homogeneous distribution after incubation with 400 mg/dL glucose solution, confirming the glucose-triggered insulin release. See FIG. 3E.

The quick release of insulin was obtained after exposure to a high glucose solution due to the dissociation of d-GRPs, while only a small amount of released insulin was observed in the control sample under 0 or 100 mg/dL glucose levels. See FIGS. 5A and 5B. Furthermore, a pulsatile release profile of insulin was achieved when d-GRPs were alternatively immersed in the normal and hyperglycemic solutions for several cycles. See FIG. 5C.

The release rates changed in response to the change of glucose levels, indicating the disassociation of d-GRPs, and the amount of insulin released was dependent on the glucose concentration. Additionally, the insulin itself was not denature during the encapsulation or release procedures; the secondary conformational structure, measured using circular dichroism, of released insulin from d-GRPs did not change compared to that of the native insulin.

Figure 6A:
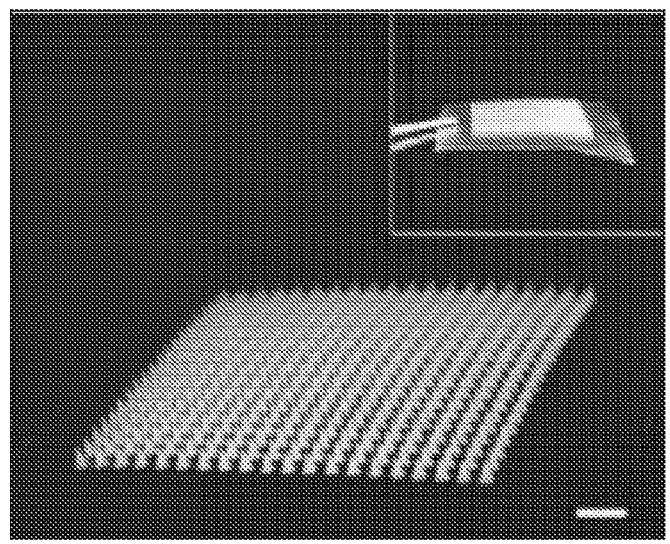
FIG. 6A is a microcopy image of a microneedle array patch comprising dual-sensitive glucose-responsive polymersomes (d-GRPs). The scale bar in the lower right represents 1 millimeter (mm). The inset shows a photograph showing the patch not under magnification.
Figure 6B:
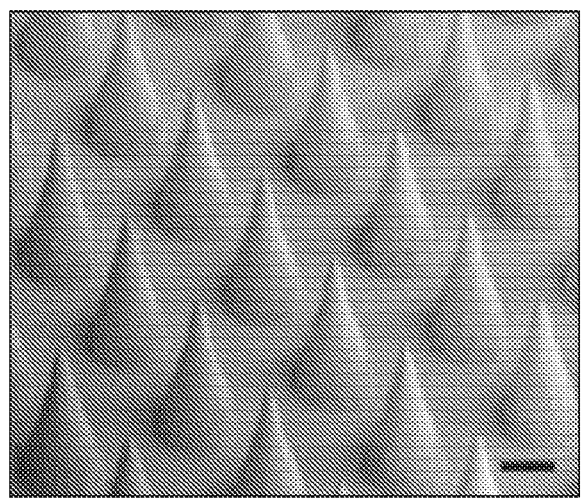
FIG. 6B is a scanning electron microscopy (SEM) image of the patch described in FIG. 6A. The scale bar in the lower right of the image represents 200 micrometers (μm).
Figure 6C:
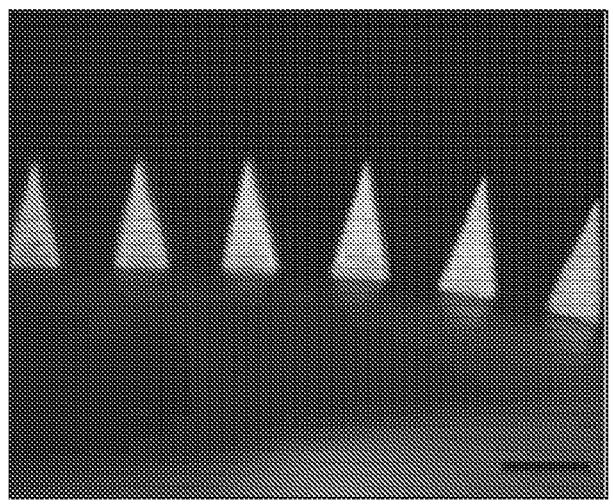
FIG. 6C is a fluorescence microscopy image of rhodamine-labelled microneedles (MN) loaded with dual-sensitive glucose-responsive polymersomes (d-GRPs) comprising fluorescein isothiocyante (FITC)-labeled insulin. The scale bar in the bottom right of the image represents 500 micrometers (μm).

To achieve convenient and painless administration, d-GRPs were integrated with a crosslinked MN-array patch composed of crosslinked hyaluronic acid using a micromolding approach. See FIG. 8. The resulting MNs were arranged in a 20×20 array, and each needle was of conical shape, with diameters of about 300 μm at the base and about 10 μm at the tip and a height of about 600 μm. See FIGS. 6A and 6B. The fluorescence image in FIG. 6C displays a representative rhodamine-labelled MN with FITC-insulin-loaded d-GRPs, indicating d-GRPs were well distributed in the tip region of each needle. The mechanical strength of the MN was measured as 3 N/needle using a tensile compression machine, which was sufficient for skin insertion without breaking. See Prausnitz, Adv. Drug Deliv., Rev., 2004, 56(5), 581-587.

Next, in vivo efficacy of the patch for diabetes treatment was assessed using streptozotocin-induced adult type 1 diabetic C57BL/6J mice. The diabetic mice were randomly divided into four groups (n=5) and the following patches transcutaneously attached: the empty MNs containing only cross-linked HA, MNs loaded with human recombinant insulin, MNs loaded with d-GRPs encapsulating GOx and insulin [d-GRP(E+I)], and MNs loaded with d-GRPs encapsulating insulin only [d-GRP(I)] (insulin dose: 10 mg/kg). The trypan blue staining of needle penetration sites was clearly observed on the excised skin sample, and the hematoxylin and eosin (H&E)-stained slide further verified that MNs could easily penetrate to the epidermis, which exposed the d-GRPs to the interstitial fluid. After removal of the MNs, the punctures in the skin rapidly disappeared and were not evident at 4 h.

The BGLs of each group were closely monitored after administration. As shown in FIG. 6D, a rapid decline of BGLs was observed in the group treated with d-GRP(E+I)-loaded MNs in the first 1 h, and the BGLs maintained in a normal state for up to 6 h without peaks of hypoglycemia. In contrast, without the enzyme GOx, the BGLs of mice treated with d-GRP(I)-loaded MNs did not show an obvious decrease, indicating that d-GRPs were stable in normal tissues. Correspondingly, the plasma human insulin levels in mice treated with d-GRP(E+I)-loaded MNs were higher than those treated d-GRP(I)-loaded MNs for at least 24 h. See FIG. 6E.

To further investigate the in vivo glucose control capability of MNs, an additional administration with MNs was performed 2.5 hour post the first administration. Unlike the group administered with free insulin-loaded MNs, the BGLs of the mice administered with d-GRP(E+I)-loaded MNs did not further decline to a hyperglycemic state (see FIG. 6F), supporting the idea that these smart insulin patches can efficiently avoid a risk of hypoglycemia. Further, the application of an additional patch was able to prolong the treatment efficacy in response to the elevated BGLs compared to one patch.

Figure 6G:
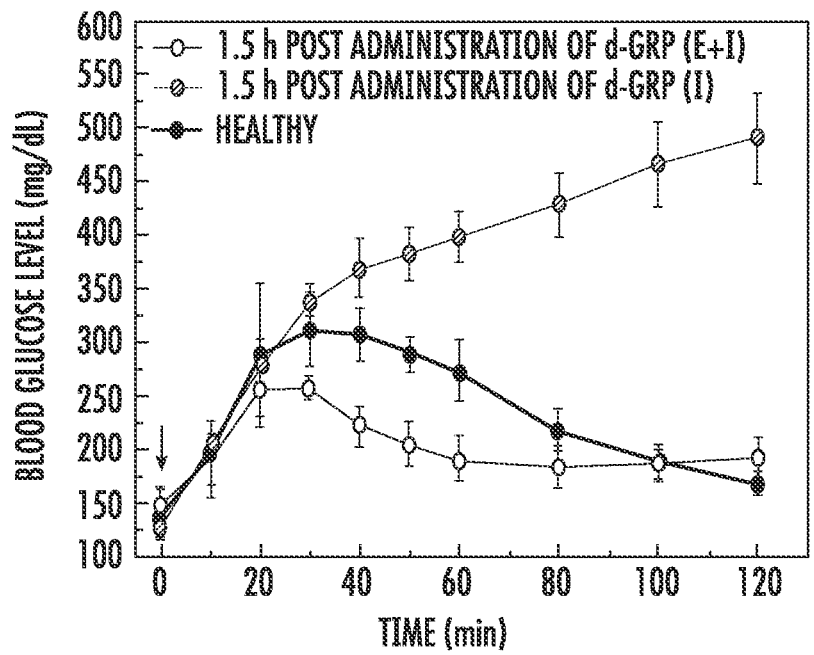
FIG. 6G is a graph of data obtained in an in vivo blood glucose tolerance test in diabetic mice one and one half hours post administration of a dual-sensitive glucose-responsive polymersome (d-GRP)-loaded microneedle (MN) array patch where the d-GRPs contained insulin and glucose oxidase enzyme (i.e., d-GRP(E+I), open circles). For comparison, data is also shown for healthy mice (filled circles) and for diabetic mice one hour post administration of an MN array patch where the MNs are loaded with d-GRPs containing only insulin (d-GRP(I), striped circles).
Figure 6H:
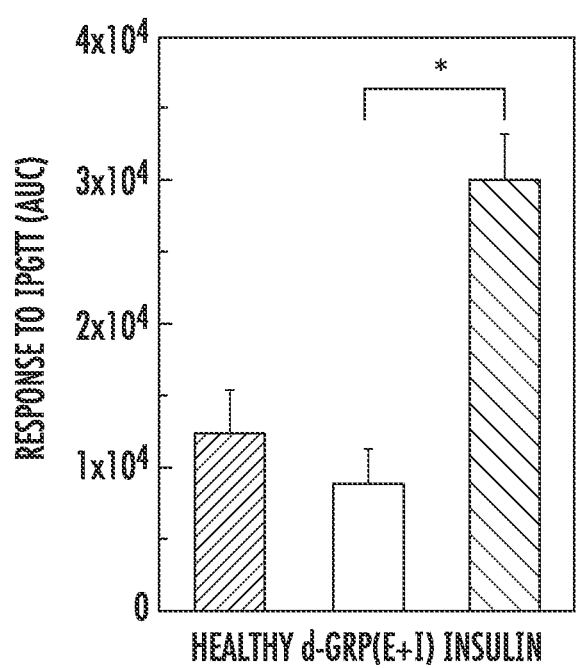
FIG. 6H is a graph showing responsiveness to intraperitoneally injected glucose in mice from the test described for FIG. 6G, calculated based on the area under the curve (AUC) in 120 minutes, with the baseline set at the zero-minute glucose reading. $*p<0.05$ for administration with dual-sensitive glucose-responsive polymersomes (d-GRP) containing insulin and glucose oxidase enzyme (d-GRP(E+I))-loaded microneedles (MNs) compared with administration of MNs comprising d-GRPs containing insulin only.

Next, an intraperitoneal glucose tolerance test (IPGTT) (see Chou et al, Proc. Natl. Acad. Sci. USA, 112(8), 2401-2406) was performed at 1.5 h after administration of MNs in order to further evaluate the dynamic of insulin release in vivo. The BGLs of diabetic mice treated with d-GRP(E+I)-loaded MNs showed a relatively delayed increase after glucose injection, and then declined to a normoglycemic state within 60 min. See FIG. 6G. In contrast, the mice treated with insulin-loaded MNs showed a gradual increase in blood glucose in 120 min. To quantitate the glucose response to the various MNs, the area under the curve was calculated between 0 and 120 min for each group. As shown, the d-GRP(E+I)-loaded administered mice showed enhanced glucose responsiveness to the glucose challenge. See FIG. 6H.

Figure 6I:
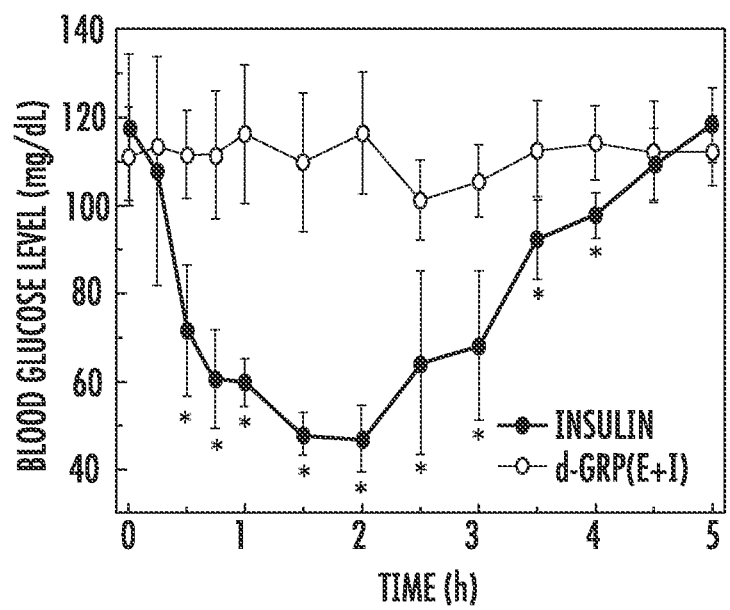
FIG. 6I is a graph showing blood glucose changes in healthy mice treated with a microneedle (MN) array patch as a function of time from 0 to 5 hours. The MN patch was loaded with dual-sensitive glucose-responsive polymersomes (d-GRPs) loaded with insulin and glucose oxidase enzyme (i.e., d-GRP(E+I), open circles). For comparison, blood glucose changes are also shown for healthy mice treated with a MN array patch loaded with insulin only (Insulin, filled circles). $*p<0.05$ for administration with dual-sensitive glucose-responsive polymersomes (d-GRP) containing insulin and glucose oxidase enzyme (d-GRP(E+I))-loaded microneedles (MNs) compared with administration of MNs containing insulin only.
Figure 6J:
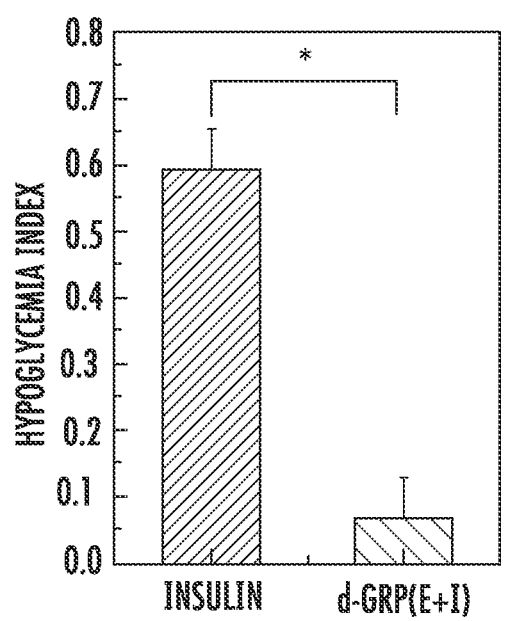
FIG. 6J is a graph of the quantification of the hypoglycemic index of the mice described for FIG. 6I. The hypoglycemic index was calculated from the difference between the initial and nadir blood glucose readings divided by the time at which nadir was reached. $*p<0.05$ for administration with a dual-sensitive glucose-responsive polymersome (d-GRP) microneedle (MN) array patch containing d-GRPs loaded with enzyme and insulin (d-GRP(E+I)) compared with an insulin-loaded MN array patch (Insulin). Error bars indicate s.d. (n=5).

To examine the potential for induction of hypoglycemia by MNs further, we studied their effect on the healthy mice. As shown in FIG. 6I, the insulin-loaded MNs produced reduced BGLs compared to d-GRP(E+I)-loaded MNs-treated mice, indicating that there was little insulin leak in d-GRP-loaded MNs. The corresponding hypoglycemia index was calculated to measure the risk of hypoglycemia. d-GRPs-loaded MNs exhibited a reduced hypoglycemia index compared to the free insulin-loaded MNs. See FIG. 6J.

Figure 7:
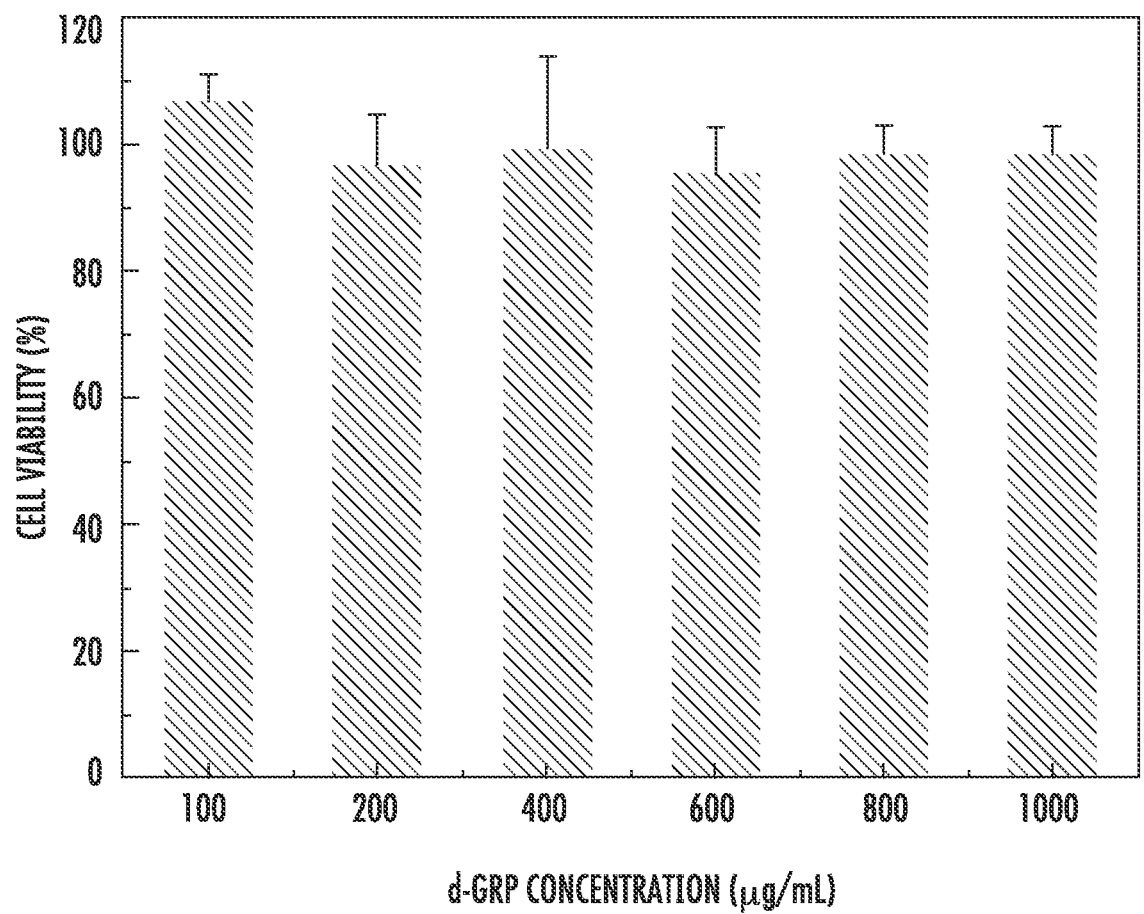
FIG. 7 is a graph showing the cell viability of HeLa cells after 24 hours incubation with different concentrations (100, 200, 400, 600, 800, or 1000 micrograms per milliliter (μg/mL)) of dual-sensitive glucose-responsive polymersomes (d-GRPs). Error bars indicate s.d. (n=6).

To study the biocompatibility of MNs loaded with d-GRPs, both d-GRPs-loaded MNs and GRPs-loaded MNs without $H_2O_2$ eliminating ability were transcutaneously attached to a single mouse at different sites. Meanwhile, the pure hyaluronic acid MNs were attached to the same mouse as a negative control. Under a high GOx dose (3 mg/kg), skin damage was observed at the site where GRP(E)-loaded MNs had been attached for two days, while there were no significant lesions at the sites treated with d-GRP(E)-loaded MNs or pure hyaluronic acid MNs. The histological images using H&E staining showed that GRP(E)-loaded MNs caused neutrophil infiltration, indicating a pathophysiological response and tissue damage induced by the generated $H_2O_2$. In contrast, no significant pathological abnormalities occurred in the site treated with d-GRP(E)-loaded MNs. Moreover, the skin tissue stained with the in situ terminal deoxyribonucleotidyl transferase (TDT)-mediated dUTP-digoxigenin nick end labeling (TUNEL) assay showed the cell apoptosis in the skin sample treated with GRP(E)-loaded MNs, whereas no cell death in the skin tissue treated with the d-GRP(E)-loaded MNs and pure hyaluronic acid MNs. The cytotoxicity of bare d-GRPs toward HeLa cells was evaluated by 3-(4,5)-dimethylthiahiazo(-z-yl)-3,5-diphenytetrazoliumromide (MTT) assay. As presented in FIG. 7, the bare d-GRPs did not show significant toxicity within all the studied concentrations.

In summary, an effective glucose-responsive insulin delivery strategy has been developed utilizing vesicles sensitive to both hypoxia and $H_2O_2$. A local hypoxic environment can be quickly generated due to oxygen consumption during the enzymatic conversion of glucose to gluconic acid, which can facilitate the solubility switch of the polymer through the bioreduction of NI groups on the side chains. Moreover, the thioether moiety within the designed polymer not only responds to $H_2O_2$, the byproduct during glucose oxidation, to promote the disassembly of vesicles, but can also eliminate the excess $H_2O_2$ to maintain the activity of GOx and circumvent damage to skin tissue. Furthermore, the d-GRPs can be integrated within a cross-linked HA-based MN-array patch to achieve convenient, painless and continuous administration of insulin. The in vivo studies demonstrated that this SIP was effective in tight regulation of BGLs in diabetic mice and showed minimal side effects. Additionally, this dual-sensitive formulation strategy displays the potential benefit of controlled delivery for other therapeutic agents under hypoxia and high oxidative stress.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:
1. A composition comprising:
   (a) an amphiphilic polymeric material comprising a polymer conjugated to a hydrogen peroxide-sensitive hydrophobic group and a hypoxia-sensitive hydrophobic group, wherein said hydrogen peroxide-sensitive group comprises a hydrogen peroxide-sensitive moiety that can be oxidized in the presence of hydrogen peroxide to form a hydrophilic moiety and said hypoxia-sensitive hydrophobic group comprises a hypoxia-sensitive moiety that can be reduced in the presence of a hypoxic environment to form a hydrophilic moiety;
   (b) an insulin or a bioactive derivative thereof; and
   (c) a glucose oxidizing agent.
2. The composition of claim 1, wherein the polymer is biodegradable.
3. The composition of claim 1, wherein the polymer comprises a diblock copolymer.
4. The composition of claim 1, wherein the polymer comprises a polyamino acid; a poly(ethylene glycol)(PEG); or a combination thereof.

5. The composition of claim 1, wherein the hydrogen peroxide-sensitive moiety comprises a thioether.

6. The composition of claim 1, wherein the hypoxia-sensitive moiety comprises a nitroimidazole.

7. The composition of claim 1, wherein the hydrogen peroxide-sensitive hydrophobic group and/or the hypoxia-sensitive hydrophobic group is covalently bound to the polymer.

8. The composition of claim 1, wherein said amphiphilic polymeric material comprises poly(ethylene glycol) (PEG) and polyserine modified with 2-nitroimidazole via a thioether moiety.

9. The composition of claim 1, wherein the glucose oxidizing agent is glucose oxidase (GOx).

10. The composition of claim 1, wherein the insulin is selected from a human insulin, a recombinant human insulin, insulin from a non-human animal, a fast-acting insulin, a rapid-acting insulin analog, an intermediate-acting insulin, and/or a long-acting insulin.

11. The composition of claim 1, wherein the insulin is recombinant human insulin.

12. The composition of claim 1, wherein the amphiphilic polymeric material forms a vesicle encapsulating said insulin or bioactive derivative thereof and said glucose oxidizing agent.

13. A nanoparticle comprising the composition of claim 1.

14. A vesicle comprising an amphiphilic polymeric material, wherein the amphiphilic polymeric material comprises a polymer conjugated to a hydrogen peroxide-sensitive hydrophobic group and a hypoxia-sensitive hydrophobic group, wherein said hydrogen peroxide-sensitive group comprises a hydrogen peroxide-sensitive moiety that can be oxidized in the presence of hydrogen peroxide to form a hydrophilic moiety and said hypoxia-sensitive hydrophobic group comprises a hypoxia-sensitive moiety that can be reduced in the presence of a hypoxic environment to form a hydrophilic moiety, and further wherein (i) an insulin or a bioactive derivative thereof and (ii) a glucose oxidizing agent are contained within said vesicle.

15. The vesicle of claim 14, wherein the polymer comprises a polyamino acid; a poly(ethylene glycol)(PEG); or a combination thereof.

16. The vesicle of claim 14, wherein the hydrogen peroxide-sensitive moiety comprises a thioether.

17. The vesicle of claim 14, wherein the hypoxia-sensitive moiety comprises a nitroimidazole.

18. The vesicle of claim 14, wherein the insulin or bioactive derivative thereof is recombinant human insulin.

19. The vesicle of claim 14, wherein the glucose oxidizing agent is glucose oxidase (GOx).

20. A microneedle array comprising vesicles of claim 14, optionally wherein said microneedle array comprises a plurality of microneedles, wherein each of said plurality of microneedles has a length of between about 20 and about 1000 microns, further optionally wherein each of the plurality of microneedles has a length of about 600 microns.

21. The microneedle array of claim 20, wherein the microneedle array is provided as part of a skin patch, optionally wherein said patch comprises one or more backing layers and/or skin-compatible adhesives.

22. A closed-loop insulin delivery system comprising a microneedle array of claim 20.

23. A method of delivering an insulin or a bioactive insulin derivative to a subject in need thereof, the method comprising providing a microneedle array of claim 20, and applying said array to a skin surface of said subject, wherein when glucose comes into contact with the microneedle array, it is oxidized, thereby (1) creating a hypoxic environment that results in the reduction of the hypoxia-sensitive moiety to form a hydrophilic moiety and (2) producing hydrogen peroxide that results in the oxidation of the hydrogen peroxide-sensitive moiety to form a hydrophilic moiety, leading to disruption of vesicles and release of an insulin or a bioactive insulin derivative contained in the vesicles.

24. The method of claim 23, wherein the delivery of the insulin or bioactive insulin derivative is at a rate corresponding to the glucose concentration coming into contact with the microneedle array.

25. The method of claim 23, wherein the subject is a mammal.

26. The method of claim 23, wherein the subject is diabetic.

27. A method of preparing a microneedle array for the glucose-sensitive delivery of insulin or a bioactive derivative thereof, the method comprising:
(a) preparing an aqueous solution of a vesicle of claim 14;
(b) dispersing said aqueous solution into a mold comprising a plurality of microneedle cavities, thereby providing a filled mold;
(c) drying the filled mold to remove water; and
(d) removing the mold to provide a microneedle array.

28. The method of claim 27, further comprising cross-linking polymeric materials in the microneedle array.

29. The method of claim 27, wherein step (b) is performed under vacuum.

30. The method of claim 27, wherein after step (b), the mold is centrifuged to compact the vesicles into the microneedle cavities.

31. The method of claim 27, wherein step (c) is performed in a vacuum desiccator.

32. The method of claim 27, wherein the mold comprises silicone.

33. The method of claim 27, wherein the cross-linking is performed by exposure to UV irradiation.

34. The composition of claim 4, wherein the polyamino acid is polyserine.

35. The vesicle of claim 15, wherein the polyamino acid is polyserine.

* * * * *